US008137823B2

(12) United States Patent
Kim et al.

(10) Patent No.: US 8,137,823 B2
(45) Date of Patent: Mar. 20, 2012

(54) ANTHRACENE DERIVATIVES, PROCESS FOR PREPARATION THEREOF, AND ORGANIC ELECTRONIC LIGHT EMITTING DEVICE USING THE SAME

(75) Inventors: Ji-Eun Kim, Daejeon (KR); Jae-Chol Lee, Daejeon (KR); Tae-Yoon Park, Daejeon (KR); Dae-Woong Lee, Daejeon (KR); Kong-Kyeom Kim, Daejeon (KR); Sung-Kil Hong, Daejeon (KR); Hye-Young Jang, Daejeon (KR); Yeon-Hwan Kim, Goyang-si (KR); Dong-Seob Jeong, Seoul (KR)

(73) Assignee: LG Chem, Ltd., Seoul (KR)

( * ) Notice: Subject to any disclaimer, the term of this patent is extended or adjusted under 35 U.S.C. 154(b) by 170 days.

(21) Appl. No.: 11/988,794

(22) PCT Filed: Mar. 15, 2007

(86) PCT No.: PCT/KR2007/001269
§ 371 (c)(1),
(2), (4) Date: Jan. 15, 2008

(87) PCT Pub. No.: WO2007/105917
PCT Pub. Date: Sep. 20, 2007

(65) Prior Publication Data
US 2009/0079334 A1 Mar. 26, 2009

(30) Foreign Application Priority Data
Mar. 15, 2006 (KR) .................. 10-2006-0023830

(51) Int. Cl.
*H01L 51/54* (2006.01)

(52) U.S. Cl. ........ 428/690; 428/917; 313/504; 313/505; 313/506; 257/40; 257/E51.026; 257/E51.052; 564/426; 564/434

(58) Field of Classification Search .................. 428/690, 428/917; 313/504, 505, 506; 257/40, E51.026, 257/E51.052; 564/426–434
See application file for complete search history.

(56) References Cited

U.S. PATENT DOCUMENTS
2003/0072966 A1 4/2003 Hosokawa et al.
(Continued)

FOREIGN PATENT DOCUMENTS
JP 2001-131541 A 5/2001
(Continued)

OTHER PUBLICATIONS
Yamaguchi et. al., Bipolar Charge Carrier . . . Canadian J. of Chem., vol. 69, 1991, p. 759-760.*
(Continued)

*Primary Examiner* — Jennifer Chriss
*Assistant Examiner* — Gregory Clark
(74) *Attorney, Agent, or Firm* — McKenna Long & Aldridge LLP

(57) ABSTRACT

The present invention relates to a novel anthracene derivative, a process for preparation thereof, and an organic electronic device using the same. The anthracene derivative according to the present invention can serve as a hole injecting material, a hole transporting material, an electron injecting material, an electron transporting material, or a light emitting material, and particularly as a light emitting host or dopant, especially as a green host or dopant singly, in an organic electronic device including an organic light emitting device. The organic electronic device according to the present invention exhibits excellent characteristics in efficiency, drive voltage, life time, and stability.

18 Claims, 1 Drawing Sheet

U.S. PATENT DOCUMENTS

| | | | |
|---|---|---|---|
| 2005/0038296 A1* | 2/2005 | Hosokawa et al. | 564/426 |
| 2005/0260442 A1* | 11/2005 | Yu et al. | 428/690 |
| 2007/0087222 A1* | 4/2007 | Kim et al. | 428/690 |
| 2010/0001635 A1* | 1/2010 | Lee et al. | 313/504 |

FOREIGN PATENT DOCUMENTS

| | | |
|---|---|---|
| JP | 2004-091334 A | 3/2004 |
| JP | 2004-095850 A | 3/2004 |
| JP | 2006-041103 * | 2/2006 |
| KR | 1020070040528 A | 4/2007 |
| WO | WO 2007/021117 A1 | 2/2007 |

OTHER PUBLICATIONS

City Collegiate Document.*

* cited by examiner

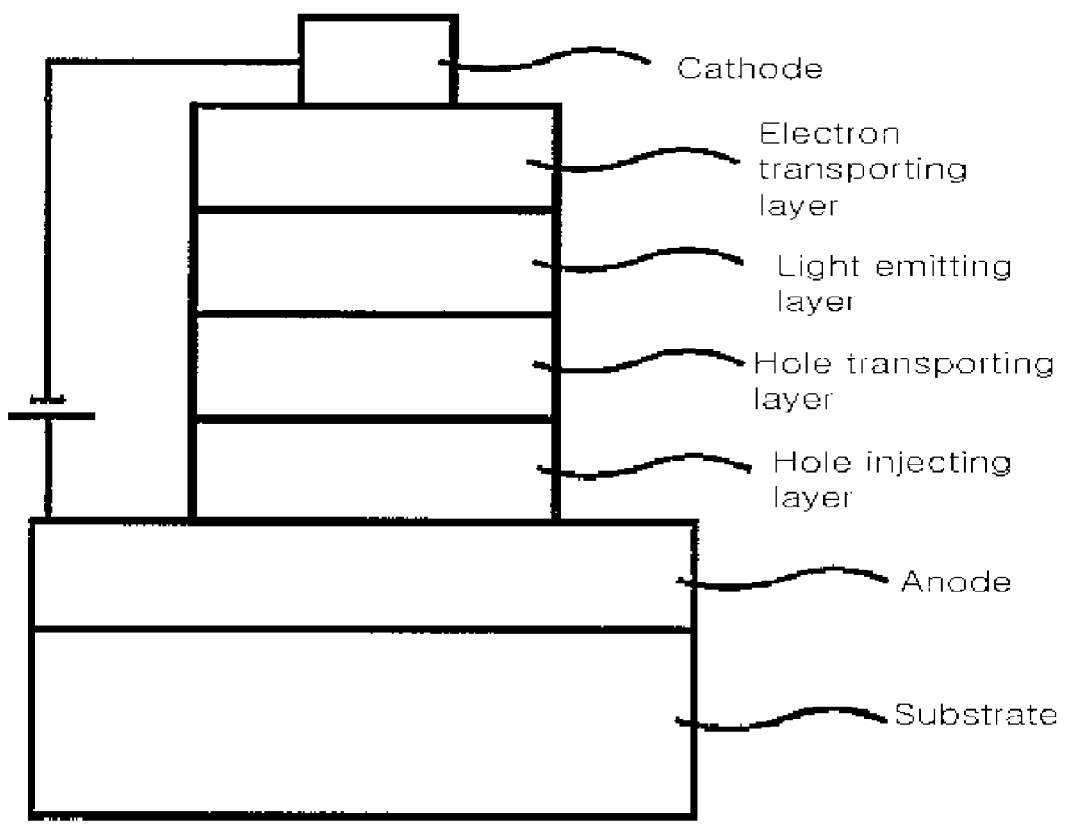

ANTHRACENE DERIVATIVES, PROCESS FOR PREPARATION THEREOF, AND ORGANIC ELECTRONIC LIGHT EMITTING DEVICE USING THE SAME

TECHNICAL FIELD

The present invention relates to a novel anthracene derivative, a process for preparation thereof, and an organic electronic light emitting device using the same.

This application claims priority benefits from Korean Patent Application No. 10-2006-0023830, filed on Mar. 15, 2006, the entire contents of which are fully incorporated herein by reference.

BACKGROUND ART

The term "organic electronic device" refers to a device requiring charge exchange between an electrode using holes and/or electrons and an organic material. The organic electronic device can be largely classified into two types according to its operational principle as follows: one type is an electronic device having a configuration in which an exciton is formed in an organic material layer by photons flown from an external light source into the device and the exciton is separated into an electron and a hole, the electron and the hole formed are transported to a different electrode, respectively and used as a current source (voltage source), and the other type is an electronic device having a configuration in which a hole and/or electron are/is injected into an organic material semiconductor forming an interface with an electrode by applying a voltage or current to two or more electrodes to allow the device to operate by means of the injected electron and hole.

Examples of the organic electronic device include an organic light emitting device, an organic solar cell, an organic photoconductor (OPC) and an organic transistor, all of which require a hole injecting or hole transporting material, an electron injecting or electron transporting material, or a light emitting material for driving the device.

Hereinafter, the organic light emitting device will be mainly and specifically described, but in the above-mentioned organic electronic devices, the hole injecting or hole transporting material, the electron injecting or electron transporting material, or the light emitting material injection functions according to a similar principle.

In general, the term "organic light emitting phenomenon" refers to a phenomenon in which electric energy is converted to light energy by means of an organic material. The organic light emitting device using the organic light emitting phenomenon has a structure usually comprising an anode, a cathode and organic material layers interposed therebetween. Herein, the organic material layer may be mostly formed in a multilayer structure comprising layers of different materials, for example, the hole injecting layer, the hole transporting layer, the light emitting layer, the electron transporting layer, the electron injecting layer and the like, in order to improve efficiency and stability of the organic light emitting device. In the organic light emitting device having such a structure, when a voltage is applied between two electrodes, holes from the anode and electrons from a cathode are injected into the organic material layer, the holes and the electrons injected are combined together to form excitons. Further, when the excitons drop to a ground state, lights are emitted. Such the organic light emitting device is known to have characteristics such as self-luminescence, high brightness, high efficiency, low drive voltage, wide viewing angle, high contrast, and high-speed response.

The materials used for the organic material layer in the organic light emitting device can be classified into a light emitting material and a charge transporting material, for example, a hole injecting material, a hole transporting material, an electron transporting material, and an electron injecting material, according to their functions. The light emitting material can be divided into a high molecular weight type and a low molecular weight type according to their molecular weight, and divided into a fluorescent material from singlet excited states and a phosphorescent material from triplet excited states according to their light emitting mechanism. Further, the light emitting material can be divided into blue, green and red light emitting materials, and yellow and orange light emitting materials required for giving more natural color, according to a light emitting color.

On the other hand, an efficiency of a device is lowered owing to maximum luminescence wavelength moved to a longer wavelength due to the interaction between the molecules, the deterioration of color purity and the reduction in light emitting efficiency when only one material is used for the light emitting material, and therefore a host/dopant system can be used as the light emitting material for the purpose of enhancing the color purity and the light emitting efficiency through energy transfer. It is based on the principle that if a small amount of a dopant having a smaller energy band gap than a host which forms a light emitting layer, excitons which are generated in the light emitting layer are transported to the dopant, thus emitting a light having a high efficiency. Here, since the wavelength of the host is moved according to the wavelength of the dopant, a light having a desired wavelength can be obtained according the kind of the dopant.

In order to allow the organic light emitting device to fully exhibit the above-mentioned excellent characteristics, a material constituting the organic material layer in the device, for example, a hole injecting material, a hole transporting material, a light emitting material, an electron transporting material, and an electron injecting material should be essentially composed of a stable and efficient material. However, the development of a stable and efficient organic material layer material for the organic light emitting device has not yet been fully realized. Accordingly, the development of new materials is continuously desired. The development of such a material is equally required to the above-mentioned other organic electronic devices.

DISCLOSURE

Technical Problem

Thus, the present inventors have synthesized a novel anthracene derivative, and then have found that this compound can exhibit effects of increased efficiency, lower drive voltage, increased life time, and higher stability, when used as a light emitting host or dopant in a light emitting layer of an organic electronic device, thus completing the present invention.

Technical Solution

Therefore, it is an object of the present invention to provide a novel anthracene derivative.

It is another object of the present invention to provide a process for preparing the anthracene derivative.

It is still another object of the present invention to provide an organic electronic device using the anthracene derivative.

Advantageous Effects

The anthracene derivative according to the present invention can serve as a hole injecting material, a hole transporting material, an electron injecting material, an electron transporting material, or a light emitting material, and particularly as a light emitting host or dopant, especially as a green host or dopant singly, in an organic electronic device including an organic light emitting device. The organic electronic device according to the present invention exhibits excellent characteristics in efficiency, drive voltage, life time, and stability.

DESCRIPTION OF DRAWINGS

FIG. 1 is a diagram illustrating the structure of the organic light emitting device according to one embodiment of the present invention.

BEST MODE

The present invention provides an anthracene derivative represented by the following formula 1:

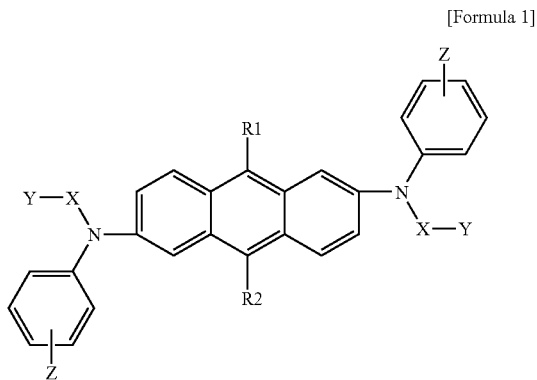

[Formula 1]

wherein

R1 and R2 are each independently a $C_6$ to $C_{20}$ aryl group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group which is substituted with deuterium, a $C_8$ to $C_{20}$ arylalkenyl group, a substituted or unsubstituted silane group, a substituted or unsubstituted boron group, a substituted or unsubstituted germanium group, and a substituted or unsubstituted $C_5$ to $C_{20}$ heterocyclic group; a $C_5$ to $C_{20}$ heterocyclic group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkylthio group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group which is substituted with deuterium, a substituted or unsubstituted silane group, a substituted or unsubstituted boron group, a substituted or unsubstituted germanium group, and a substituted or unsubstituted $C_5$ to $C_{20}$ heterocyclic group; or a condensed ring group of a $C_6$ to $C_{20}$ aromatic ring and a $C_4$ to $C_{20}$ aliphatic ring, X's may be the same or different from each other, and are each independently a $C_6$ to $C_{20}$ arylene group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group which is substituted with deuterium, a substituted or unsubstituted silane group, a substituted or unsubstituted boron group, a substituted or unsubstituted germanium group, and a substituted or unsubstituted $C_5$ to $C_{20}$ heterocyclic group; or a divalent $C_5$ to $C_{20}$ heterocyclic group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkylthio group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group which is substituted with deuterium, a substituted or unsubstituted silane group, a substituted or unsubstituted boron group, and a substituted or unsubstituted germanium group, and a substituted or unsubstituted $C_5$ to $C_{20}$ heterocyclic group, Y is hydrogen, deuterium, halogen, CN, $NO_2$, a $C_1$ to $C_{20}$ alkyl group, a $C_1$ to $C_{20}$ alkoxy group, a $C_1$ to $C_{20}$ alkylamine group, a $C_6$ to $C_{20}$ arylamine group, a $C_1$ to $C_{20}$ alkyl thio group, a $C_6$ to $C_{20}$ aryl thio group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group which is substituted with deuterium, a substituted or unsubstituted silane group, a substituted or unsubstituted boron group, a substituted or unsubstituted germanium group, or a substituted or unsubstituted $C_5$ to $C_{20}$ heterocyclic group, and Z is CN, $NO_2$, deuterium, a $C_1$ to $C_{20}$ alkyl thio group, a $C_6$ to $C_{20}$ aryl thio group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a substituted or unsubstituted silane group, a substituted or unsubstituted boron group, or a substituted or unsubstituted germanium group.

In the formula 1, R1 and R2 are preferably each independently a phenyl group, a phenyl group which is substituted with a substituted or unsubstituted $C_5$ to $C_{20}$ heterocyclic group, a phenyl group which is substituted with five deuteriums, a naphthyl group, a biphenyl group, a fluorenyl group, an anthracenyl group, a tetracenyl group, a pentacenyl group, a terphenyl group, a tetralinyl group, a stilbenzyl group, a carbazolylene group, a perylenyl group, a pyrenyl group, a phenanthrenyl group, a triphenylenyl group, a crycenyl group, a pyridyl group, a bipyridyl group, a carbazole group, a thiophenyl group, a quinolinyl group, or an isoquinolinyl group, but are not limited thereto.

In the formula 1, X's may be the same or different from each other, and are preferably each independently a phenylene group, a phenylene group which is substituted with a substituted or unsubstituted $C_5$ to $C_{20}$ heterocyclic group, a phenylene group which is substituted with deuterium, a naphthylene group, a biphenylene group, a fluorenylene group, an anthracenylene group, a tetracenylene group, a pentacenylene group, a terphenylene group, a tetralinylene group, a stilbenzylene group, a carbazolylene group, a perylenylene group, a pyrenylene group, a phenathrenylene group, a triphenylenylene group, a crycenylene group, a pyridylene group, a bipyridylene group, a carbazole group, a thiophenylene group, a quinolinylene group, or an isoquinolinylene group, but are not limited thereto.

In the formula 1, Y is preferably hydrogen, deuterium, a $C_6$ to $C_{20}$ aryl group which is substituted with deuterium, a substituted or unsubstituted silane group, a substituted or unsubstituted boron group, or a substituted or unsubstituted germanium group, a substituted or unsubstituted $C_5$ to $C_{20}$ heterocyclic group, or a $C_6$ to $C_{20}$ aryl group, but is not limited thereto.

In the formula 1, Z is preferably CN, $NO_2$, deuterium, a substituted or unsubstituted silane group, or a substituted or unsubstituted germanium group, but is not limited thereto.

In the formula 1, if R1, R2, X, and Z have different substituents, these substituents can be selected from the group consisting of an alkyl group, an alkoxy group, an alkenyl group, an aryl group, an aryl amine group, a heterocyclic group, a silane group, a boron group, an aliphatic ring group, an amino group, a nitrile group, a nitro group, a halogen group, an amide group, an ester group, and an ether group.

Specific examples of the anthracene derivative of the formula 1 according to the present invention are shown as follows, but are not limited thereto.

[Compound 1]

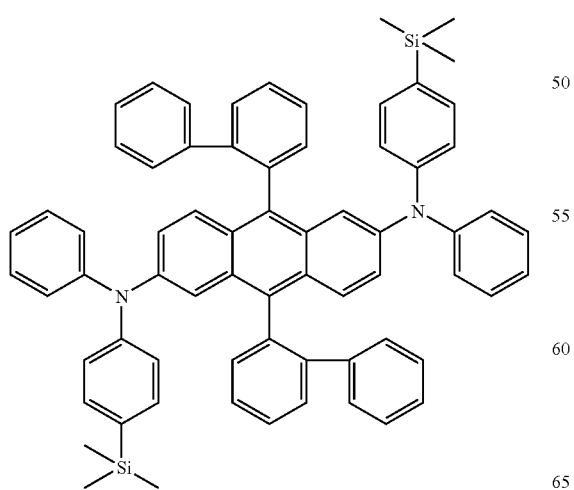

[Compound 2]

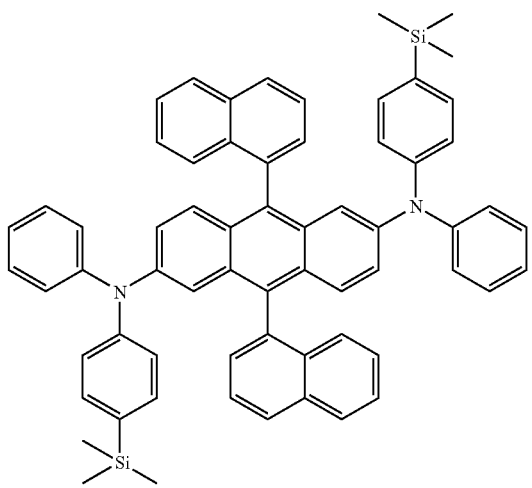

[Compound 3]

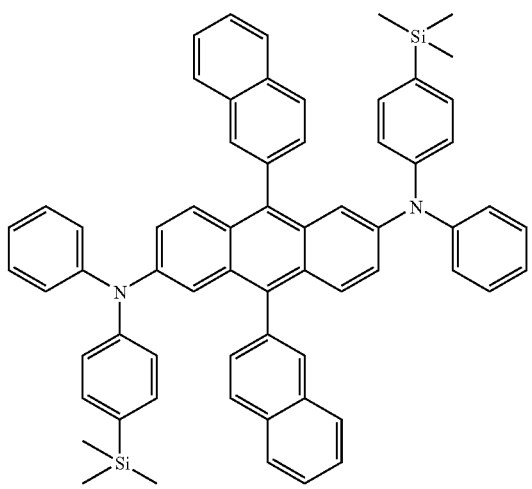

[Compound 4]

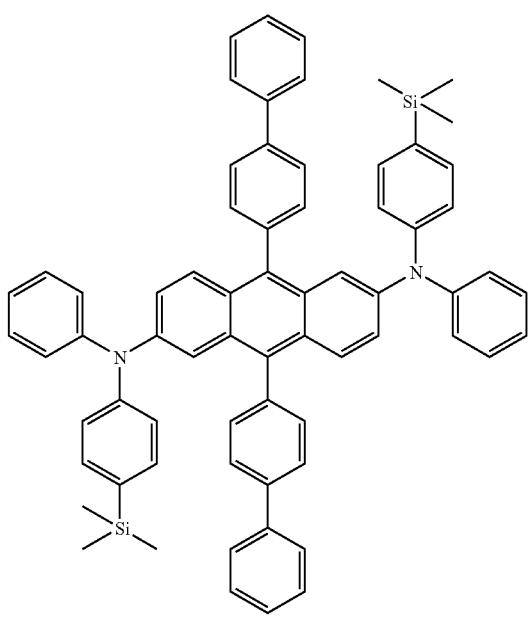

[Compound 5]
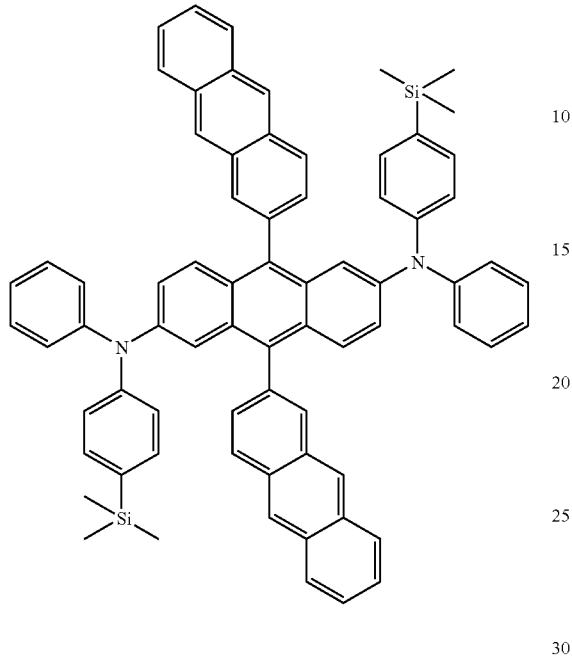
[Compound 6]
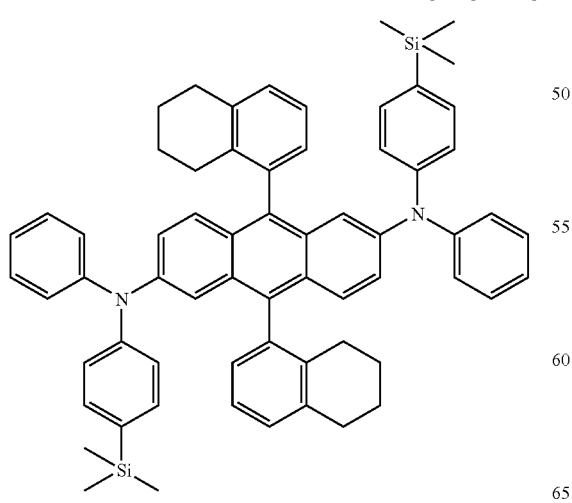
[Compound 7]
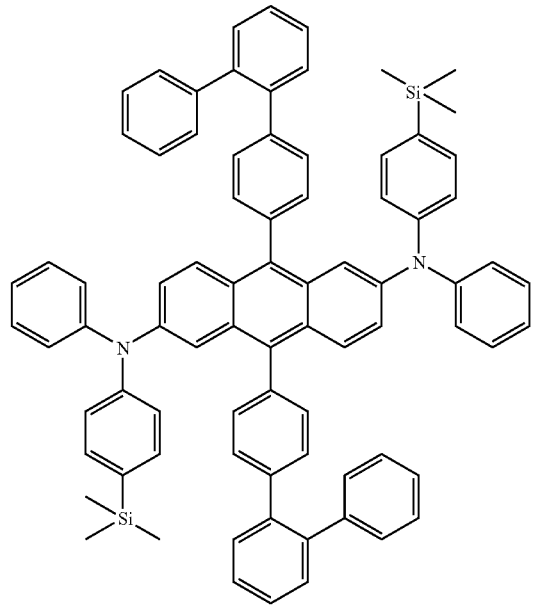
[Compound 8]
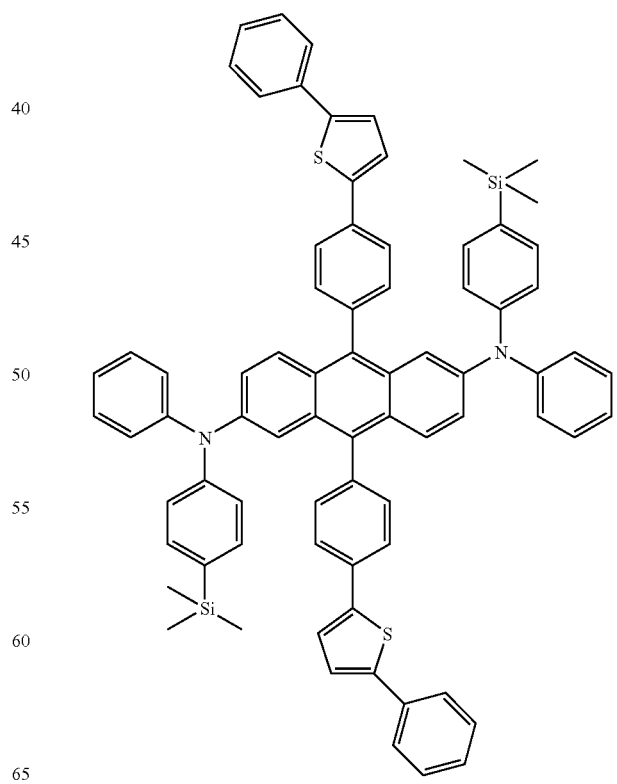

[Compound 9]
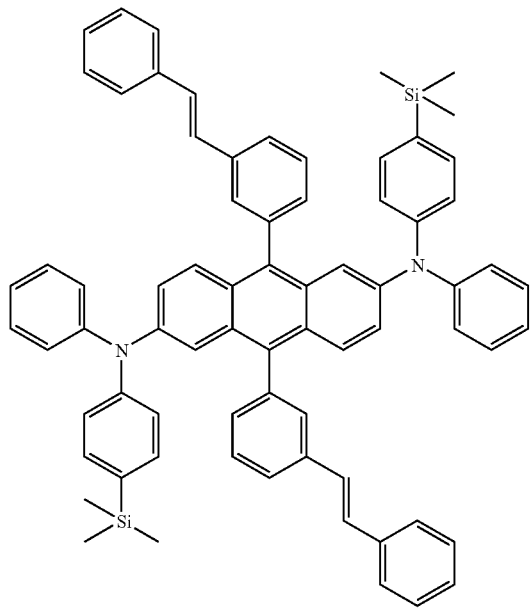
[Compound 11]
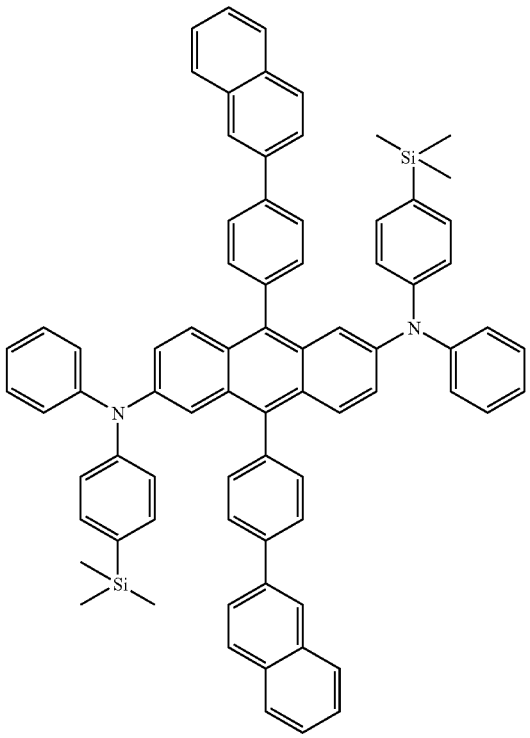
[Compound 10]
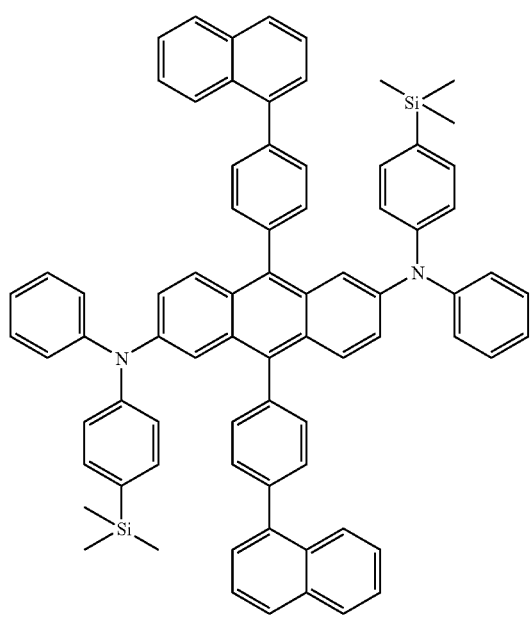
[Compound 12]
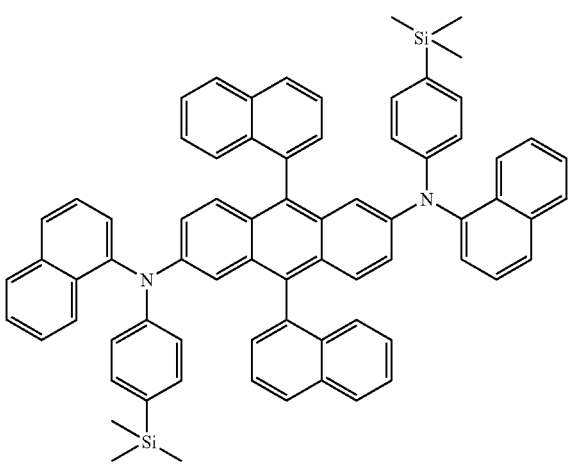

[Compound 13]
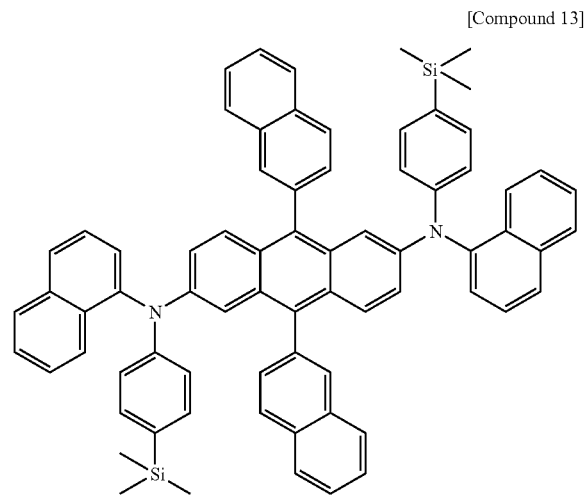
[Compound 14]
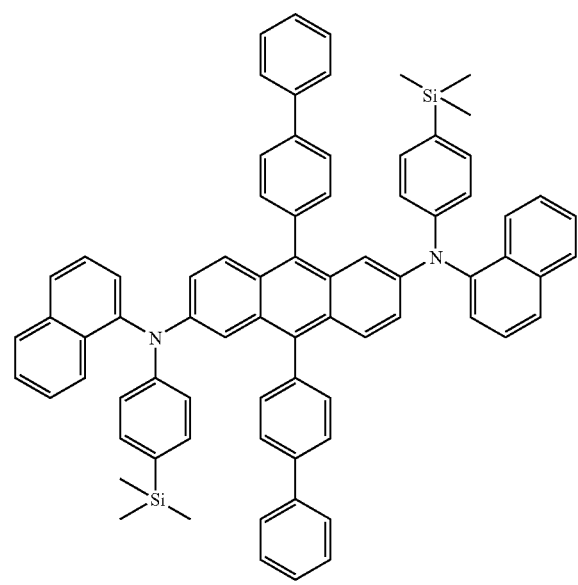
[Compound 15]
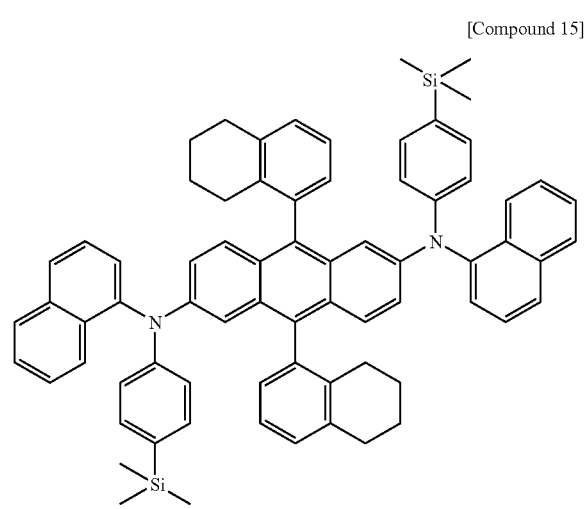
[Compound 16]
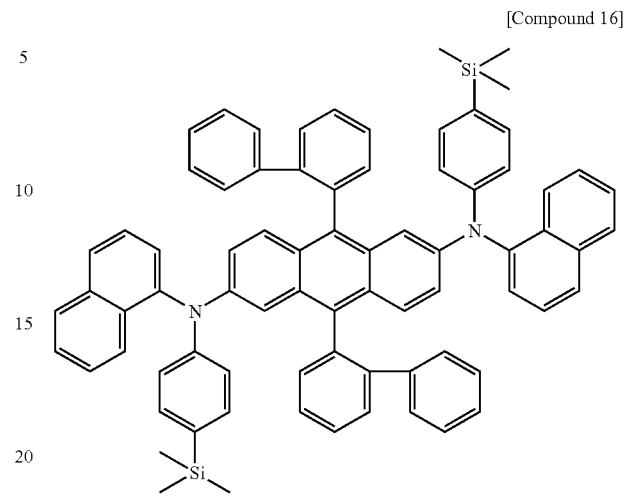
[Compound 17]
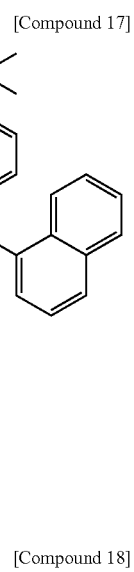
[Compound 18]
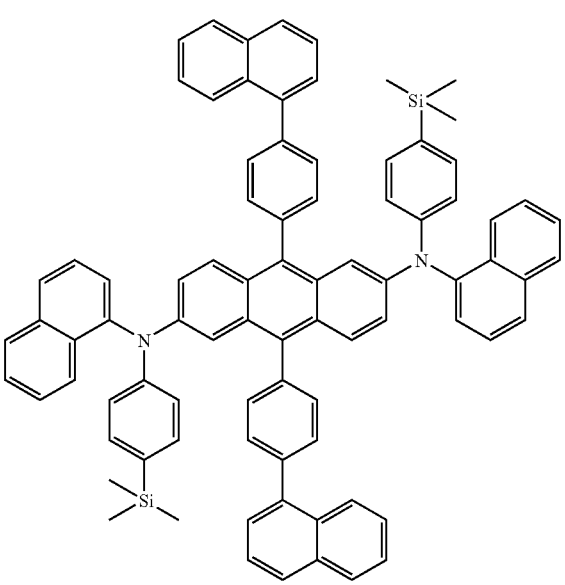

[Compound 19]
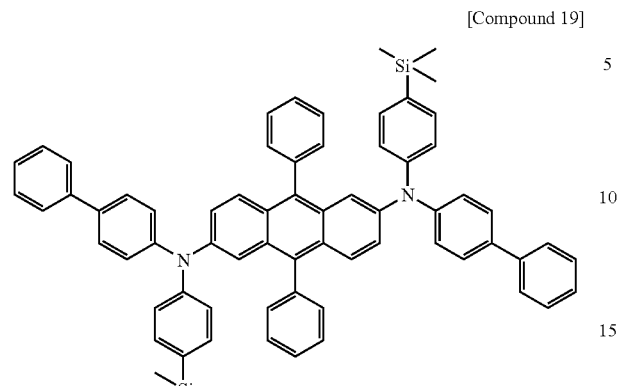
[Compound 20]
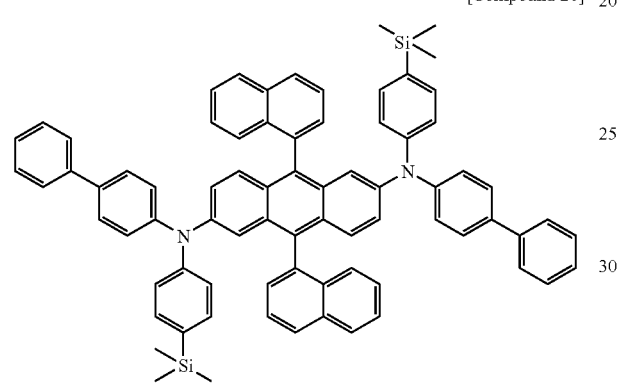
[Compound 21]
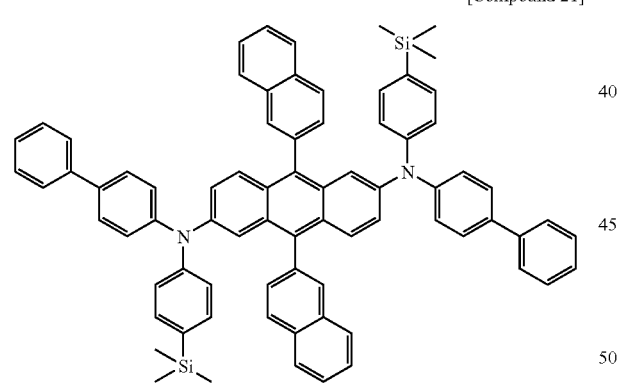
[Compound 22]
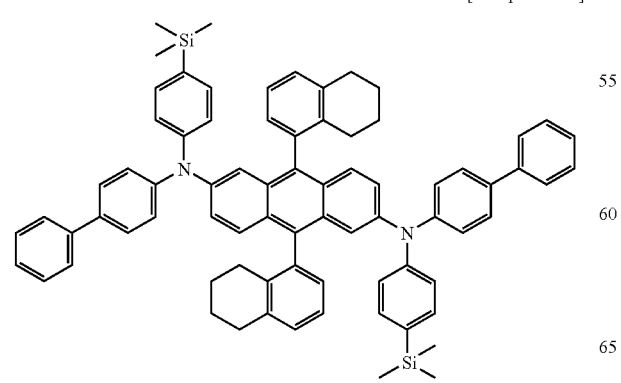
[Compound 23]
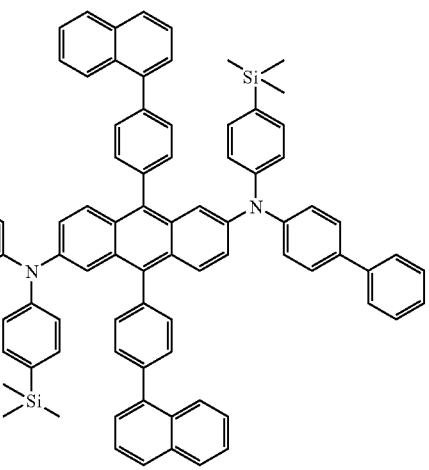
[Compound 24]
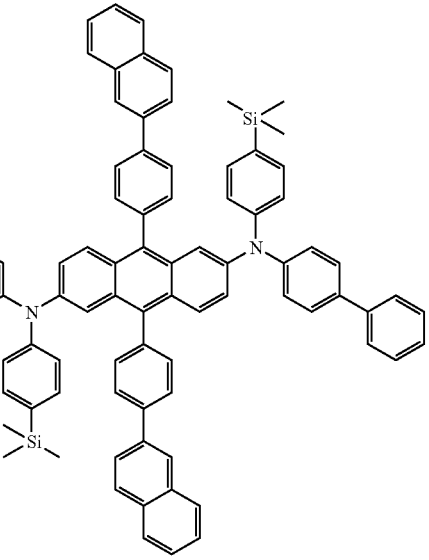
[Compound 25]
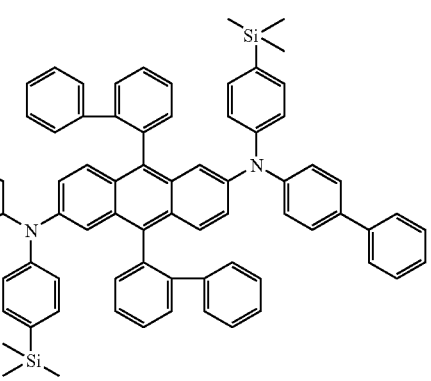

[Compound 26]
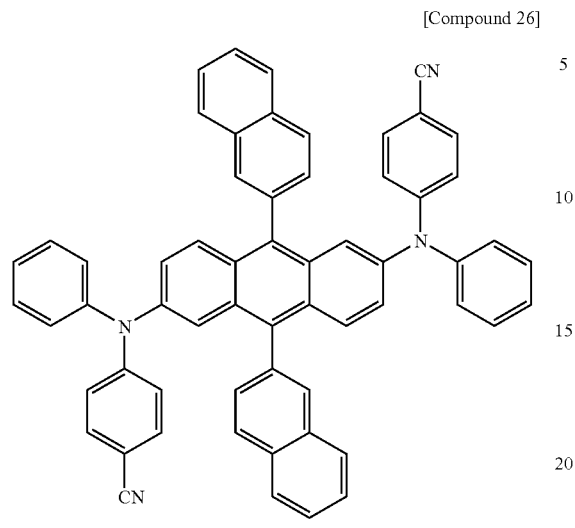
[Compound 27]
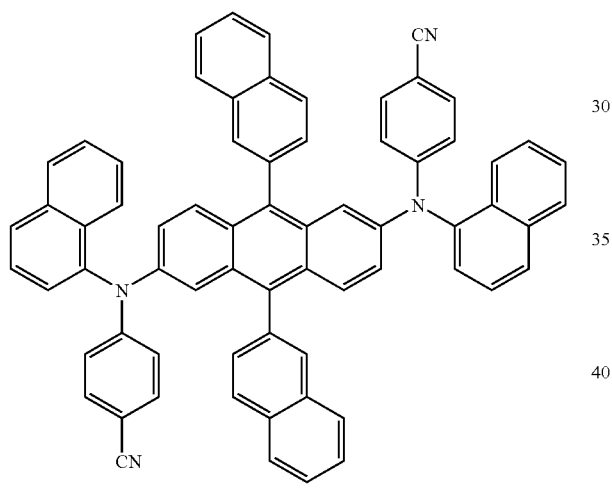
[Compound 28]
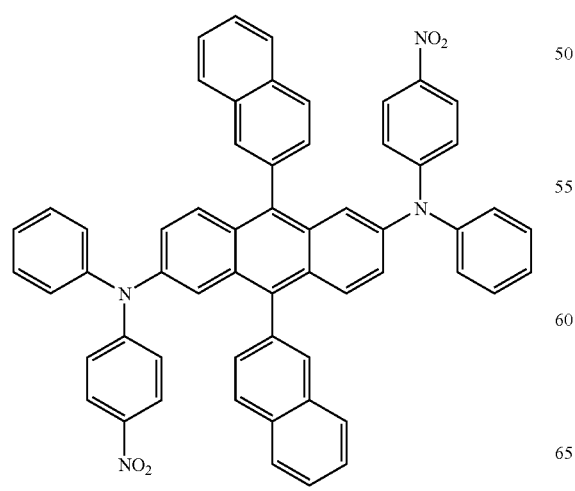
[Compound 29]
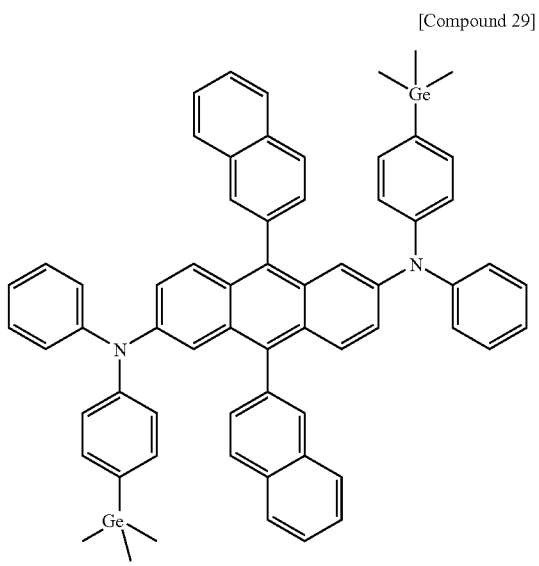
[Compound 30]
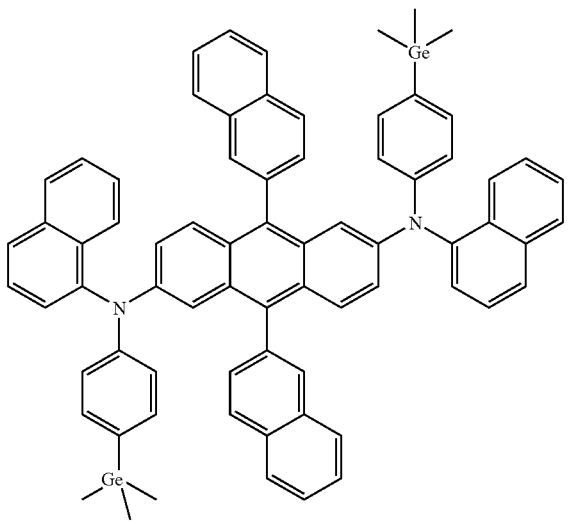
[Compound 31]
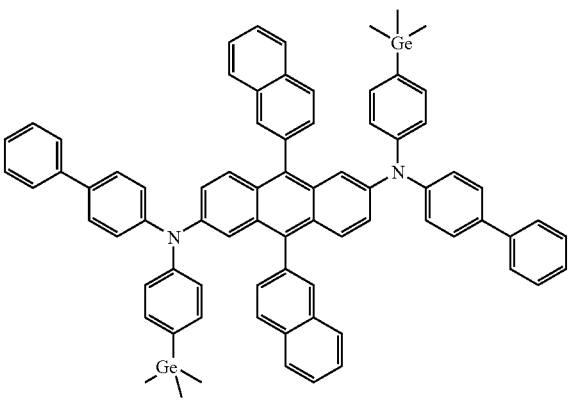

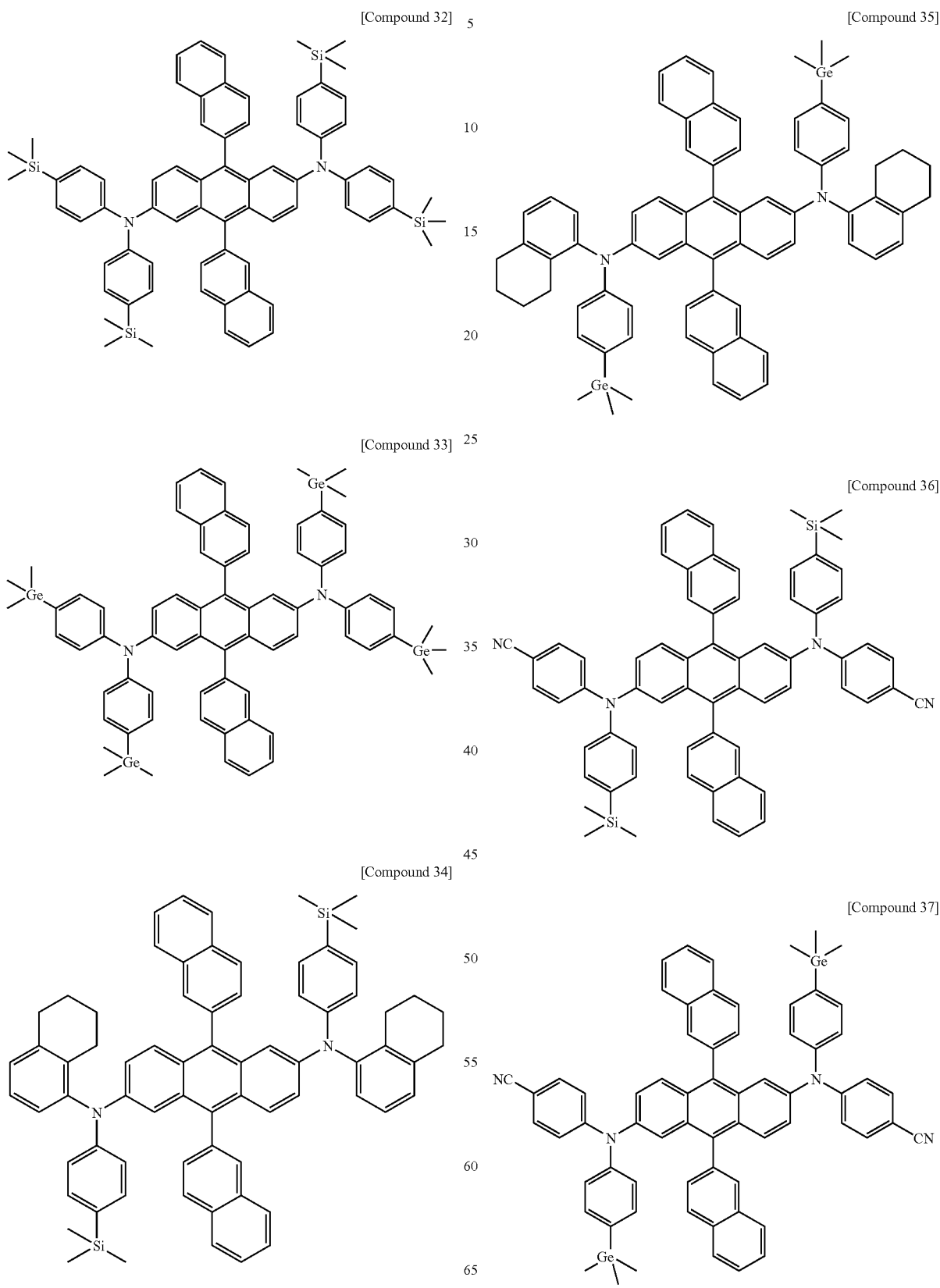

[Compound 38]
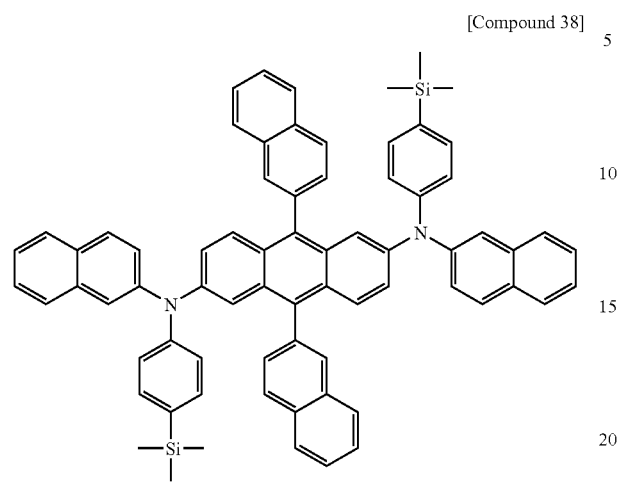
[Compound 39]
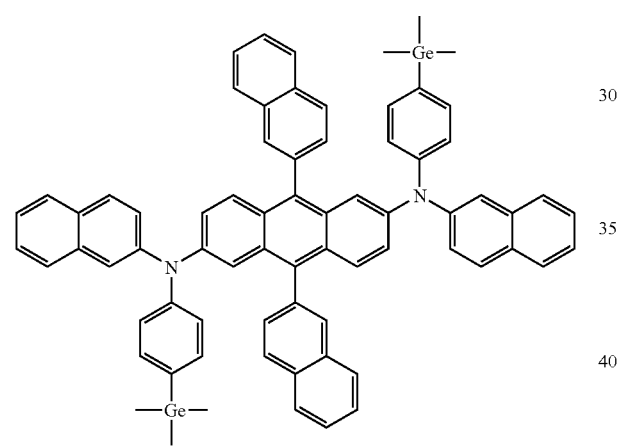
[Compound 40]
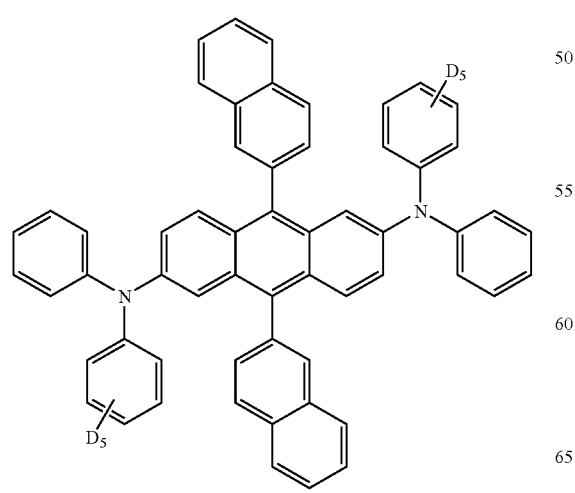
[Compound 41]
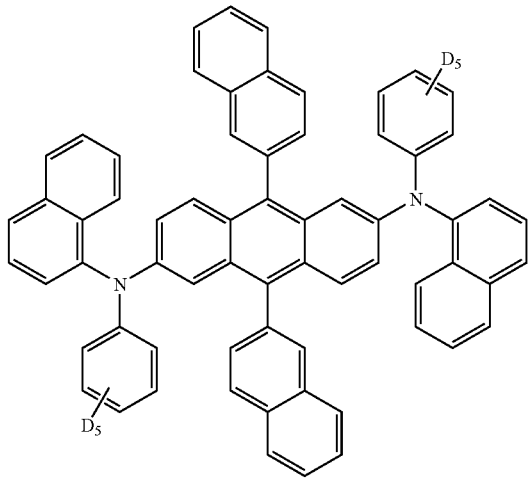
[Compound 42]
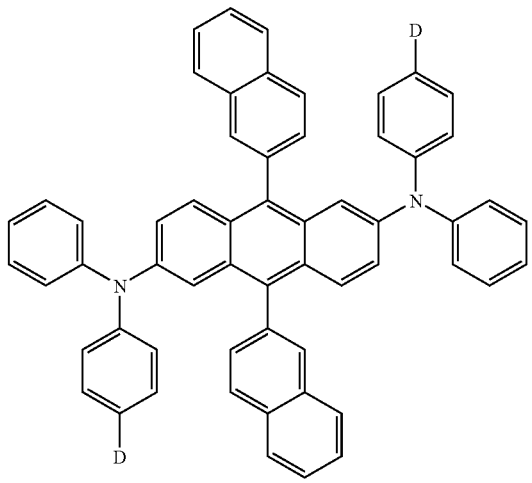
[Compound 43]
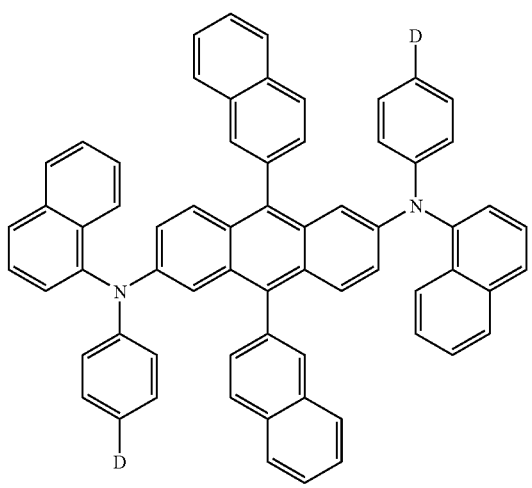

[Compound 44]

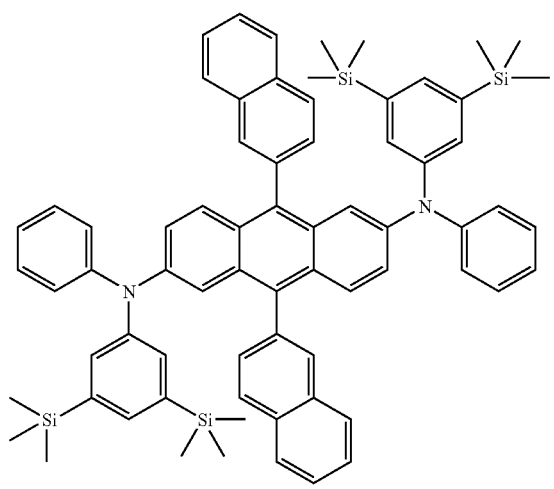

[Compound 45]

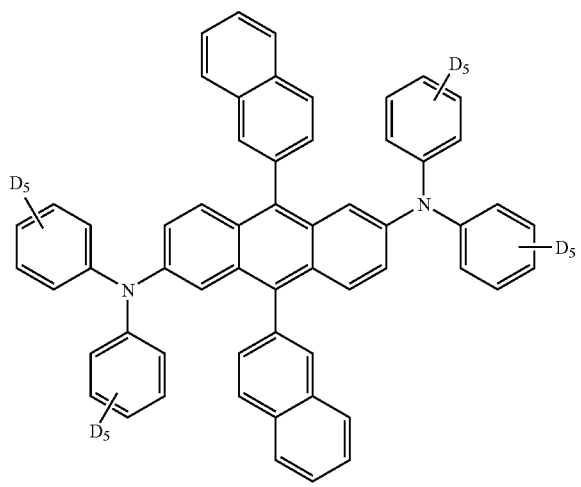

[Compound 46]

of Examples as below. As will be clear in Examples, the certain intermediate compounds are first synthesized, and then the compounds of the formula 1 are prepared from the intermediate compounds. Some exemplary intermediate compounds are listed below as Compounds A to Q. In these compounds, "Br" may be substituted with any other reactive atoms or functional groups.

[Compound A]

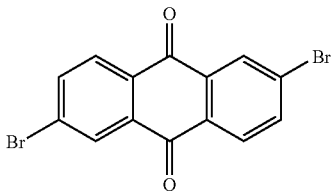

[Compound B]

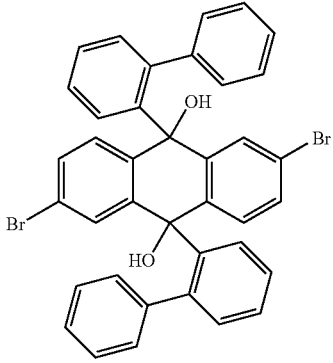

[Compound C]

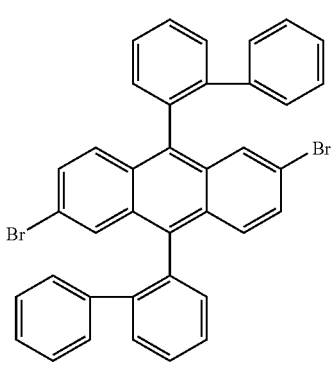

[Compound D]

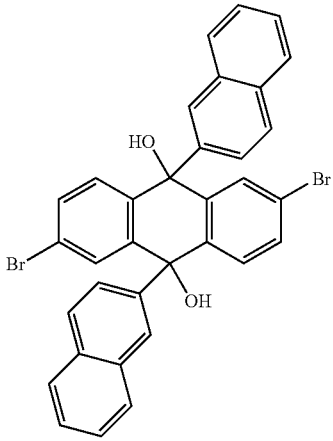

Further, the present invention provides a process for preparing the anthracene derivative represented by the formula 1.

The anthracene derivative according to the present invention can be prepared by reacting a dibromoaryl compound with an arylamine compound in the presence of a palladium catalyst.

The arylamine compound preferably contains a silyl group, deuterium, or a germanium group.

The compounds of the formula 1 according to the present invention can be synthesized in multi-step chemical reactions. The syntheses of the compounds are described by way

[Compound E]

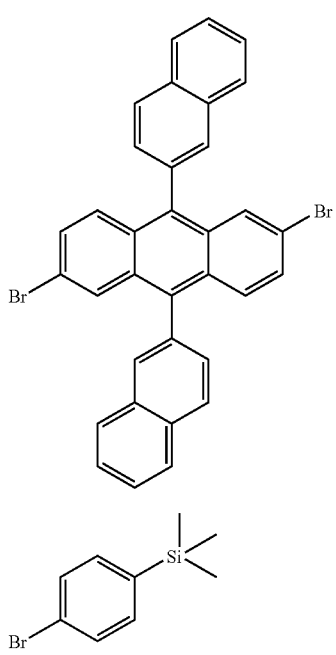

[Compound F]

[Compound G]

[Compound H]

[Compound I]

[Compound J]

[Compound K]

[Compound L]

[Compound M]

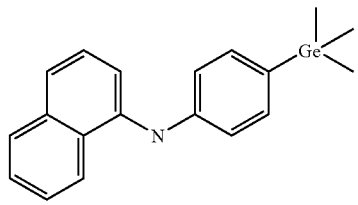

[Compound N]

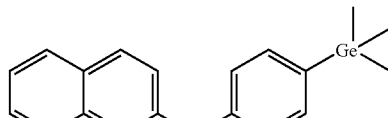

[Compound O]

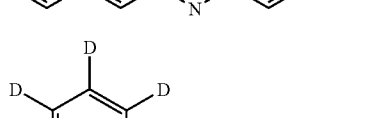

[Compound P]

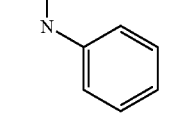

[Compound Q]

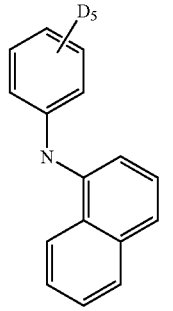

Further, the present invention provides an organic electronic device using the compound of the formula 1.

The organic electronic device of the present invention can be prepared by usual methods and materials for preparing an organic electronic device, except that the above-described compounds are used to form one or more organic material layers.

Hereinbelow, the organic light emitting device will be exemplified.

The above-described compounds of the present invention can serve as a hole injecting material, a hole transporting material, an electron injecting, electron transporting, or a light emitting material, and particularly serve alone as a light emitting material, as well as a light emitting host with an appropriate light emitting dopant or a light emitting dopant with an appropriate light emitting host in an organic light emitting device.

In another embodiment of the present invention, the organic light emitting device may be the structure that comprises a first electrode, a second electrode and organic material layers interposed therebetween, and can be prepared by usual methods and materials for preparing an organic light emitting device, except that the above-described compound according to the present invention is used to form at least one layer of the organic material layers in an organic light emitting device. The structure of the organic light emitting device of the present invention can be shown in FIG. 1.

For example, the organic light emitting device according to the present invention can be prepared by depositing a metal, a metal oxide having conductivity or an alloy thereof on a substrate using a PVD (physical vapor deposition) process such as sputtering and e-beam evaporation to form an anode; forming an organic material layer comprising a hole injecting layer, a hole transporting layer, a light emitting layer, and an electron transporting layer on the anode; and depositing a material, which can be used as a cathode, thereon. Alternatively, an organic light emitting device can be prepared by sequentially depositing a cathode material, an organic material layer, and an anode material on a substrate.

The organic material layer may have a multilayer structure containing a hole injecting layer, a hole transporting layer, a light emitting layer, an electron transporting layer, and the like, but not limited thereto, and may have a monolayer structure. Further, the organic material layer can be produced to have a fewer number of layers, by using a variety of polymeric materials, by means of a solvent process rather than a deposit process, such as spin coating, dip coating, doctor blading, screen printing, ink jet printing, and heat transfer processes.

The anode material is preferably a material having a large work function to facilitate hole injection usually to the organic material layers. Specific examples of the anode material which can be used in the present invention include metals such as vanadium, chromium, copper, zinc and gold, or an alloy thereof; metal oxides such as zinc oxide, indium oxide, indium-tin oxide (ITO), and indium zinc oxide (IZO); a combination of a metal and an oxide, such as $ZnO:Al$ and $SnO_2:Sb$; conductive polymers such as poly(3-methylthiophene), poly[3,4-(ethylene-1,2-dioxy)thiophene] (PEDT), polypyrrole and polyaniline, but are not limited thereto.

The cathode material is preferably a material having a small work function to facilitate electron injection usually to an organic material layer. Specific examples of the cathode material include metals such as magnesium, calcium, sodium, potassium, titanium, indium, yttrium, lithium, gadolinium, aluminum, silver, tin and lead, and an alloy thereof; and multilayered materials such as LiF/Al and $LiO_2$/Al, but are not limited thereto.

The hole injecting material is a material facilitating hole injection from an anode at low voltage. The HOMO (highest occupied molecular orbital) of the hole injecting material is preferably located between the work function of the anode materials and the HOMO level of its neighboring organic material layer. Specific examples of the hole injecting material include metal porphyrin, oligothiophene, organic materials of arylamine series, hexanitrile hexaazatriphenylene, organic materials of quinacridone series, organic materials of perylene series, anthraquinone, and conductive polymers of polyaniline series and polythiophene series, but are not limited thereto.

The hole transporting material is a material having high hole mobility, which can transfer holes from the anode or the hole injecting layer toward the light emitting layer. Specific examples thereof include organic materials of arylamine series, conductive polymers, and block copolymers having both of the conjugated portions and the non-conjugated portions, but are not limited thereto.

The light emitting material are a material capable of emitting visible light by accepting and recombining holes from the hole transporting layer and electrons from the electron transporting layer, preferably a material having high quantum efficiency for fluorescence and phosphorescence. Specific examples thereof include 8-hydroxyquinoline aluminum complex ($Alq_3$); compounds of carbazole series; dimerized styryl compounds; BAlq; 10-hydroxybenzoquinoline-metal compounds; compounds of benzoxazole, benzthiazole and benzimidazole series; polymers of poly(p-phenylenevinylene) (PPV) series; Spiro compounds; and polyfluorene and rubrene compounds, but are not limited thereto.

The electron transporting material is suitably a material having high electron mobility, which can easily receive electrons from the cathode and then transfer them to the light emitting layer. Specific examples thereof include an 8-hydroxyquinoline aluminum complex; complexes including $Alq_3$; organic radical compounds; and hydroxyflavone-metal complexes, but are not limited thereto.

The organic light emitting device according to the present invention may be of a front-sided, back-sided, or double-sided light emission according to the materials used.

The compound according to the invention can also function in an organic electronic device including an organic solar cell, an organic photoconductor, and an organic transistor, according to a principle similar to that applied to the organic light emitting device.

Mode for Invention

Hereinafter, preferable Examples are provided for the purpose of making the present invention more understandable. As such, Examples are provided for illustrating the invention, but the scope of the invention is not limited thereto.

Preparative Example 1

Preparation of Compound A 2,6-Diaminoanthraquinone (23.8 g, 100 mmol) was dispersed in 48 wt % of a hydrogen bromide aqueous solution. Sodium nitrite ($NaNO_2$, 14.1 g, 204 mmol) was slowly added to the mixture at −20° C., which evolved nitrogen gas. After gas evolution was completed, a solution of copper bromide (CuBr, 29.5 g, 206 mmol) dissolved in 48 wt % of a hydrogen bromide aqueous solution (63 mL) was slowly added to the mixture together with a small amount of ethanol (50 mL). The temperature of the resulting mixture was slowly elevated and then the mixture was slowly refluxed. The mixture was cooled to room temperature and was diluted with water. The precipitate in the mixture was filtered off with suction, washed with water, and dried in vacuo. The dried precipitate was dissolved in chloroform, filtered through silica gel, and concentrated under reduced pressure. The residue was purified by column chromatography and recrystallized from chloroform to obtain Compound A (10.0 g, 27%).

$^1$H NMR (300 MHz, $CDCl_3$), 8.44 (d, J=2.1 Hz, 2H), 8.18 (d, J=8.0 Hz, 2H), 7.95 (dd, J=2.1, 8.0 Hz, 2H).

Preparative Example 2

Preparation of Compound B

2-Bromo biphenyl (8.83 mL, 51.2 mmol) was dissolved in dry tetrahydrofuran (THF, 200 mL) under a nitrogen atmosphere at room temperature. The solution was cooled to −78° C. t-Butyl lithium (60 mL, 1.7 M pentane solution) was slowly added to the solution at −78° C., and the resulting mixture was stirred for about 40 minutes at the same temperature. Thereafter, Compound A (7.50 g, 20.5 mmol) was added to the mixture at the same temperature. The cooling bath was removed, and the mixture was stirred at room temperature for about 15 minutes. Thereafter, the mixture was added to diethyl ether (200 mL) and 2 N hydrochloric acid (200 mL), and was stirred at room temperature for about 40 minutes. The precipitate was filtered off with suction, and washed with water and ethyl ether. The resultant was dried to obtain Compound B (29.3 g, 85%).

Preparative Example 3

Preparation of Compound C

A mixture of Compound B (4.00 g, 5.93 mmol), potassium iodide (9.85 g, 59.3 mmol), and sodium hypophosphite hydrate (10.4 g, 98.0 mmol) was refluxed in a liquid mixture of acetic acid (80 mL) and ortho-dichlorobenzene (600 mL). The resulting mixture was cooled to room temperature. Then, the mixture was extracted with chloroform, dried over magnesium sulfate, and concentrated under reduced pressure. The concentrated solid was dissolved in chloroform, passed through silica gel, and concentrated under reduced pressure. The solid was dispersed in n-hexane, stirred and filtered, and then dried in vacuo to obtain Compound C (3.30 g, 87%) in light yellow color.
m.p. 478.1° C.;
$^1$H NMR (300 MHz, CDCl$_3$) 7.92 (d, J=7.6 Hz, 4H), 7.46 (t, J=8.0 Hz, 4H), 7.33 (t, J=7.4 Hz, 4H), 7.21 (d, J=7.6 Hz, 4H), 6.88 (dd, J=2.1, 8.6 Hz, 2H), 6.47 (d, J=2.1 Hz, 2H), 6.22 (d, J=8.6 Hz, 2H);
MS (M+)=636;
Anal. Calc'd. for $C_{38}H_{22}Br_2$: C, 71.50; H, 3.47; Br, 25.03. Found: C, 71.90; H, 3.40; Br, 25.7.

Preparative Example 4

Preparation of Compound D

The same procedure was carried out as in Preparative Example 2 except that 2-bromonaphthalene (10.6 g, 51.2 mmol) was used in stead of 2-bromobiphenyl (8.83 mL, 51.2 mmol) to obtain Compound D (28.6 g, 90%).

Preparative Example 5

Preparation of Compound E

The same procedure was carried out as in Preparative Example 3 except that Compound D (3.69 g, 5.93 mmol) was used in stead of Compound B (4.00 g, 5.93 mmol) to obtain Compound E (2.96 g, 85%) in light yellow color.
MS (M+)=588

Preparative Example 6

Preparation of Compound F

Dibromobenzene (20 g, 84.78 mmol) was dissolved in dry tetrahydrofuran (THF, 200 mL) at room temperature under a nitrogen atmosphere. The solution was cooled to −78° C. n-butyl lithium (34 mL, 2.5 M pentane solution) was added slowly to the solution at −78° C., and the temperature of the mixture was slowly raised to 0° C. for about 1 hour. To the mixture, chlorotrimethylsilane (13 ml, 101.74 mmol) was added, and the temperature of the mixture was raised to normal temperature over 1 hour. After confirmation of completion of the reaction, the mixture was extracted from ethyl acetate, dried over magnesium sulfate, and distilled off under reduced pressure to obtain Compound F (18 g, 93%).
MS (M+)=229

Preparative Example 7

Preparation of Compound G

Compound F (15 g, 65.45 mmol), aniline (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (200 mL), and the mixture was refluxed for about 3 hours. After completion of the reaction, the mixture was cooled to room temperature, and the reaction mixture was added to a mixed solution of THF and H$_2$O. The organic layer was subject to phase separation, dried over MgSO$_4$, concentrated, and then separated by column chromatography to obtain Compound G (15 g, 86%).
MS [M]=143

Preparative Example 8

Preparation of Compound H

The same procedure was carried out as in Preparative Example 7 except that 1-aminonaphthalene (10.3 g, 72 mmol) was used in stead of aniline (6.6 ml, 72 mmol) to obtain Compound H (14.8 g, 78%).
MS [M]=291

Preparative Example 9

Preparation of Compound I

The same procedure was carried out as in Preparative Example 7 except that 4-aminobiphenyl (10.3 g, 72 mmol) was used in stead of aniline (6.6 ml, 72 mmol) to obtain Compound I (15.58 g, 75%).
MS [M]=317

Preparative Example 10

Preparation of Compound J

The same procedure was carried out as in Preparative Example 6 except that trimethylgerumanium bromide (18 ml, 101.74 mmol) was used in stead of chlorotrimethylsilane (13 ml, 101.74 mmol) to obtain Compound J (20 g, 90%).
MS [M]=273

Preparative Example 11

Preparation of Compound K

The same procedure was carried out as in Preparative Example 7 except that Compound J (18 g, 65.45 mmol) was used in stead of Compound F (15 g, 65.45 mmol) to obtain Compound K (16 g, 85%).
MS [M]=286

Preparative Example 12

Preparation of Compound L

The same procedure was carried out as in Preparative Example 7 except that 2-aminonaphthalene (10.3 g, 72 mmol) was used in stead of aniline (6.6 ml, 72 mmol) to obtain Compound L (14.8 g, 78%).
MS [M]=291

Preparative Example 13

Preparation of Compound M

The same procedure was carried out as in Preparative Example 7 except that Compound J (18 g, 65.45 mmol) was used in stead of Compound F (15 g, 65.45 mmol), and 1-aminonaphthalene (10.3 g, 72 mmol) was used in stead of aniline (6.6 ml, 72 mmol) to obtain Compound M (17.6 g, 80%).
MS [M]=336

Preparative Example 14

Preparation of Compound N

The same procedure was carried out as in Preparative Example 13 except that 2-aminonaphthalene (10.3 g, 72 mmol) was used in stead of 1-aminonaphthalene (10.3 g, 72 mmol) to obtain Compound N (18 g, 82%).
MS [M]=336

Preparative Example 15

Preparation of Compound P

Compound O (6.84 ml, 65.45 mmol), aniline (6.6 ml, 72 mmol), pd(dba)$_2$ (0.125 g, 0.13 mmol), P(t-Bu)$_3$ (0.04 g, 0.2 mmol) and sodium t-butoxide (1.80 g, 18.7 mmol) were added to toluene (200 mL), and the mixture was refluxed for about 3 hours. After completion of the reaction, the mixture was cooled to room temperature, and the reaction mixture was added to a mixed solution of THF and H$_2$O. The organic layer was subject to phase separation, dried over MgSO$_4$, concentrated, and then separated by column chromatography to obtain Compound P (9.23 g, 81%).
MS [M]=174

Preparative Example 16

Preparation of Compound Q

The same procedure was carried out as in Preparative Example 15 except that 1-aminonaphthalene (10.3 g, 72 mmol) was used in stead of aniline (6.6 ml, 72 mmol) to obtain Compound Q (11 g, 75%).
MS [M]=224

Example 1

Preparation of Compound 1

Compound C (5.4 g, 8.5 mmol), Compound G (4.92 g, 20.4 mmol), pd(dba)$_2$ (0.097 g, 0.17 mmol), P(t-Bu)$_3$ (0.05 g, 0.255 mmol) and sodium t-butoxide (2.45 g, 25.5 mmol) were added to toluene (100 mL), and the mixture was refluxed for 2 hours. After completion of the reaction, the mixture was cooled to normal temperature, and the reaction mixture was added to a mixed solution of THF and H$_2$O. The organic layer was subject to phase separation, dried over MgSO$_4$, concentrated, and then separated by column chromatography to obtain Compound 1 (4.74 g, 58%).
MS [M]=960

Example 2

Preparation of Compound 16

The same procedure was carried out as in Example 1 except that Compound H (5.94 g, 20.4 mmol) was used in stead of Compound G (4.92 g, 20.4 mmol) to obtain Compound 16 (5.87 g, 65%).
MS [M]=1060

Example 3

Preparation of Compound 25

The same procedure was carried out as in Example 1 except that Compound I (6.5 g, 20.4 mmol) was used in stead of Compound G (4.92 g, 20.4 mmol) to obtain Compound 25 (5.68 g, 60%).
MS [M]=1112

Example 4

Preparation of Compound 3

The same procedure was carried out as in Example 1 except that Compound E (5.0 g, 8.5 mmol) was used in stead of compound C (5.4 g, 8.5 mmol) to obtain Compound 3 (5.02 g, 65%).
MS [M]=910

Example 5

Preparation of Compound 13

The same procedure was carried out as in Example 1 except that Compound E (5.0 g, 8.5 mmol) was used in stead of compound C (5.4 g, 8.5 mmol), and Compound H (5.94 g, 20.4 mmol) was used instead of Compound G (4.92 g, 20.4 mmol) to obtain Compound 13 (6.0 g, 70%)
MS [M]=1008

Example 6

Preparation of Compound 21

The same procedure was carried out as in Example 1 except that Compound E (5.0 g, 8.5 mmol) was used in stead of compound C (5.4 g, 8.5 mmol), and Compound I (6.48 g, 20.4 mmol) was used instead of Compound G (4.92 g, 20.4 mmol) to obtain Compound 21 (5.77 g, 64%).
MS [M]=1060

Example 7

Preparation of Compound 29

The same procedure was carried out as in Example 1 except that Compound E (5.0 g, 8.5 mmol) was used in stead of compound C (5.4 g, 8.5 mmol), and Compound K (5.83 g, 20.4 mmol) was used instead of Compound G (4.92 g, 20.4 mmol) to obtain Compound 29 (4.84 g, 57%).
MS [M]=998

Example 8

Preparation of Compound 30

The same procedure was carried out as in Example 1 except that Compound E (5.0 g, 8.5 mmol) was used in stead of compound C (5.4 g, 8.5 mmol), and Compound M (6.85 g, 20.4 mmol) was used instead of Compound G (4.92 g, 20.4 mmol) to obtain Compound 30 (4.67 g, 50%).
MS [M]=1098

Example 9

Preparation of Compound 38

The same procedure was carried out as in Example 1 except that Compound E (5.0 g, 8.5 mmol) was used in stead of compound C (5.4 g, 8.5 mmol), and Compound L (5.94 g, 20.4 mmol) was used instead of Compound G (4.92 g, 20.4 mmol) to obtain Compound 38 (4.98 g, 58%).
MS [M]=1008

Example 10

Preparation of Compound 39

The same procedure was carried out as in Example 1 except that Compound E (5.0 g, 8.5 mmol) was used in stead of compound C (5.4 g, 8.5 mmol), and Compound N (6.85 g, 20.4 mmol) was used instead of Compound G (4.92 g, 20.4 mmol) to obtain Compound 39 (5.79 g, 62%).
MS [M]=1098

Example 11

Preparation of Compound 40

Compound E (5.0 g, 8.5 mmol), Compound P (3.55 g, 20.4 mmol), pd(dba)$_2$ (0.097 g, 0.17 mmol), P(t-Bu)$_3$ (0.05 g, 0.255 mmol) and sodium t-butoxide (2.45 g, 25.5 mmol) were added to toluene (100 mL), and the mixture was refluxed for 2 hours. After completion of the reaction, the mixture was cooled to normal temperature, and the reaction mixture was added to a mixed solution of THF and H$_2$O. The organic layer was subject to phase separation, dried over MgSO$_4$, concentrated, and then separated by column chromatography to obtain Compound 40 (4.08 g, 62%).
MS [M]=774

Example 12

Preparation of Compound 41

Compound E (5.0 g, 8.5 mmol), Compound Q (4.57 g, 20.4 mmol), pd(dba)$_2$ (0.097 g, 0.17 mmol), P(t-Bu)$_3$ (0.05 g, 0.255 mmol) and sodium t-butoxide (2.45 g, 25.5 mmol) were added to toluene (100 mL), and the mixture was refluxed for 2 hours. After completion of the reaction, the mixture was cooled to normal temperature, and the reaction mixture was added to a mixed solution of THF and H$_2$O. The organic layer was subject to phase separation, dried over MgSO$_4$, concentrated, and then separated by column chromatography to obtain Compound 41 (4.31 g, 58%).
MS [M]=874

Experimental Example 1

A glass substrate (Corning 7059 glass) on which a thin film of ITO (indium tin oxide) was coated to a thickness of 1,000 Å was immersed in distilled water having a detergent dissolved therein to wash the substrate with ultrasonic waves. The detergent as used herein was a product commercially available from Fisher Co. and the distilled water was one which had been twice filtered by using a filter commercially available from Millipore Co. ITO was washed for 30 minutes, and then ultrasonic washing was repeated twice for 10 minutes by using distilled water. After the completion of washing with distilled water, ultrasonic washing was carried out by using isopropyl alcohol, acetone and methanol in this order as the solvents, followed by drying. The substrate was transported into a plasma washing machine. Using an oxygen plasma, the substrate was washed for 5 minutes, and then transported to a vacuum depositing machine.

On the ITO electrode, 3,6-bis-2-naphthylphenylamino-N-[4-(2-napthylphenyl)aminophenyl]carbazole (800 Å), 4,4'-bis[N-(1-naphthyl)-N-phenyl amino]biphenyl (NPB) (300 Å), and the compound 1 prepared in Example 1 were sequentially deposited with the following compound R (300 Å), and 9,10-bis-2-naphthyl-2-[4-(N-phenylbenzoimidazoyl)phenyl]anthracene (300 Å) was subsequently coated by thermal vacuum deposition to sequentially form a hole injecting layer, a hole transporting layer, a light emitting layer, and an electron transporting layer.

Lithium fluoride (LiF) and aluminum were sequentially deposited on the electron transporting layer to thicknesses of 12 Å and 2,000 Å, respectively, to form a cathode, thereby obtaining an organic light emitting device.

In the above process, the deposition rate of the organic material was maintained at 0.4 to 0.7 Å/sec and the deposition rate of lithium fluoride was maintained at 0.3 Å/sec and the deposition rate of aluminum was maintained at 2 Å/sec in cathode, respectively. The degree of vacuum upon deposition was maintained at $2 \times 10^{-7}$ to $5 \times 10^{-8}$ torr.

When a forward electric field of 8.0 V was applied to the organic light emitting device as prepared above, green light emission of 18.1 cd/A was observed with x=0.31 and y=0.64 based on the 1931 CIE color coordinate at a current density of 100 mA/cm$^2$.

[Compound R]

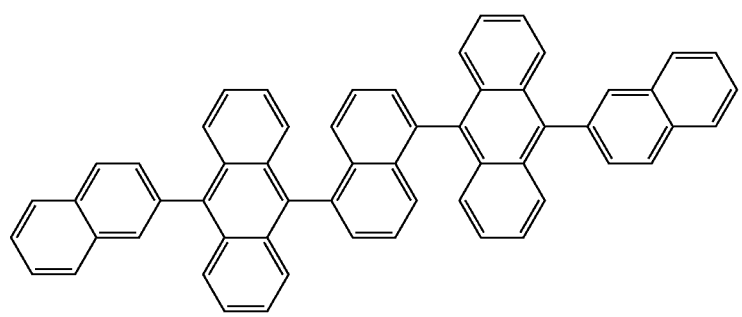

Experimental Example 2

The same procedure was carried out as in Experimental Example 1 except that Compound 3 was used in stead of Compound 1 to prepare an organic light emitting device.

When a forward electric field of 8.5 V was applied to the organic light emitting device as prepared above, green light emission of 18.5 cd/A was observed with x=0.32 and y=0.65 based on the 1931 CIE color coordinate at a current density of 100 mA/cm².

Experimental Example 3

The same procedure was carried out as in Experimental Example 1 except that Compound 13 was used in stead of Compound 1 to prepare an organic light emitting device.

When a forward electric field of 8.7 V was applied to the organic light emitting device as prepared above, green light emission of 18.1 cd/A was observed with x=0.33 and y=0.65 based on the 1931 CIE color coordinate at a current density of 100 mA/cm².

Experimental Example 4

The same procedure was carried out as in Experimental Example 1 except that Compound 16 was used in stead of Compound 1, to prepare an organic light emitting device.

When a forward electric field of 8.9 V was applied to the organic light emitting device as prepared above, green light emission of 18.5 cd/A was observed with x=0.33 and y=0.65 based on the 1931 CIE color coordinate at a current density of 100 mA/cm².

Experimental Example 5

The same procedure was carried out as in Experimental Example 1 except that Compound 21 was used in stead of Compound 1, to prepare an organic light emitting device.

When a forward electric field of 9.4 V was applied to the organic light emitting device as prepared above, green light emission of 17.8 cd/A was observed with x=0.33 and y=0.64 based on the 1931 CIE color coordinate at a current density of 100 mA/cm².

Experimental Example 6

The same procedure was carried out as in Experimental Example 1 except that Compound 25 was used in stead of Compound 1, to prepare an organic light emitting device.

When a forward electric field of 9.6 V was applied to the organic light emitting device as prepared above, green light emission of 17.9 cd/A was observed with x=0.32 and y=0.65 based on the 1931 CIE color coordinate at a current density of 100 mA/cm².

Experimental Example 7

The same procedure was carried out as in Experimental Example 1 except that Compound 29 was used in stead of Compound 1 to prepare an organic light emitting device.

When a forward electric field of 9.0 V was applied to the organic light emitting device as prepared above, green light emission of 18.0 cd/A was observed with x=0.32 and y=0.63 based on the 1931 CIE color coordinate at a current density of 100 mA/cm².

Experimental Example 8

The same procedure was carried out as in Experimental Example 1 except that Compound 30 was used in stead of Compound 1, to prepare an organic light emitting device.

When a forward electric field of 9.1 V was applied to the organic light emitting device as prepared above, green light emission of 18.2 cd/A was observed with x=0.33 and y=0.64 based on the 1931 CIE color coordinate at a current density of 100 mA/cm².

Experimental Example 9

The same procedure was carried out as in Experimental Example 1 except that Compound 38 was used in stead of Compound 1, to prepare an organic light emitting device.

When a forward electric field of 9.4 V was applied to the organic light emitting device as prepared above, green light emission of 18.3 cd/A was observed with x=0.35 and y=0.66 based on the 1931 CIE color coordinate at a current density of 100 mA/cm².

Experimental Example 10

The same procedure was carried out as in Experimental Example 1 except that Compound 39 was used in stead of Compound 1, to prepare an organic light emitting device.

When a forward electric field of 9.5 V was applied to the organic light emitting device as prepared above, green light emission of 18.4 cd/A was observed with x=0.35 and y=0.67 based on the 1931 CIE color coordinate at a current density of 100 mA/cm².

The invention claimed is:

1. An anthracene derivative represented by the following formula 1:

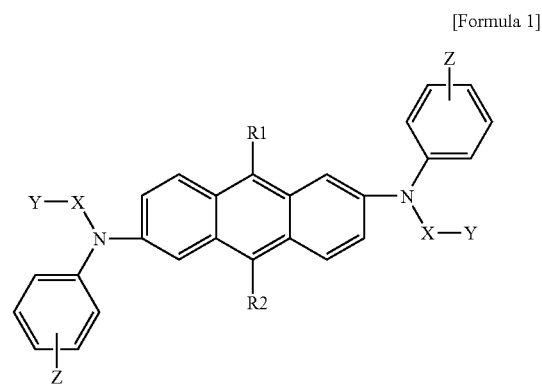

[Formula 1]

wherein

R1 and R2 are each independently a $C_6$ to $C_{20}$ aryl group which is unsubstituted or substituted with at least one selected from the group consisting of halogen, CN, $NO_2$, a $C_1$ to $C_{20}$ alkyl group, a $C_1$ to $C_{20}$ alkoxy group, a $C_1$ to $C_{20}$ alkylamine group, a $C_1$ to $C_{20}$ alkyl thiophene group, a $C_6$ to $C_{20}$ aryl thiophene group, a $C_2$ to $C_{20}$ alkenyl group, a $C_2$ to $C_{20}$ alkynyl group, a $C_3$ to $C_{20}$ cycloalkyl group, a $C_6$ to $C_{20}$ aryl group, a $C_6$ to $C_{20}$ aryl group which is substituted with deuterium, a $C_8$ to $C_{20}$ arylalkenyl group, a silane group, a boron group, a germanium group, and a $C_5$ to $C_{20}$ heterocyclic group; a $C_5$ to $C_{20}$ heterocyclic group which is unsubstituted or substituted with at least one selected from the group consisting of halogen, CN, NO$_2$, a C$_1$ to C$_{20}$ alkyl group, a C$_1$ to C$_{20}$ alkoxy group, a C$_1$ to C$_{20}$ alkylamine group, a C$_1$ to C$_{20}$ alkylthio group, a C$_2$ to C$_{20}$ alkenyl group, a C$_2$ to C$_{20}$ alkynyl group, a C$_3$ to C$_{20}$ cycloalkyl group, a C$_6$ to C$_{20}$ aryl group, a C$_6$ to C$_{20}$ aryl group which is substituted with deuterium, a silane group, a boron group, a germanium group, and a C$_5$ to C$_{20}$ heterocyclic group; or a condensed ring group of a C$_6$ to C$_{20}$ aromatic ring and a C$_4$ to C$_{20}$ aliphatic ring, X's may be the same or different from each other, and are each independently a C$_6$ to C$_{20}$ arylene group which is unsubstituted or substituted with at least one selected from the group consisting of halogen, CN, NO$_2$, a C$_1$ to C$_{20}$ alkyl group, a C$_1$ to C$_{20}$ alkoxy group, a C$_1$ to C$_{20}$ alkylamine group, a C$_1$ to C$_{20}$ alkyl thiophene group, a C$_6$ to C$_{20}$ aryl thiophene group, a C$_2$ to C$_{20}$ alkenyl group, a C$_2$ to C$_{20}$ alkynyl group, a C$_3$ to C$_{20}$ cycloalkyl group, a C$_6$ to C$_{20}$ aryl group, a C$_6$ to C$_{20}$ aryl group which is substituted with deuterium, a silane group, a boron group, a germanium group, and a C$_5$ to C$_{20}$ heterocyclic group; or a divalent C$_5$ to C$_{20}$ heterocyclic group which is unsubstituted or substituted with at least one selected from the group consisting of halogen, CN, NO$_2$, a C$_1$ to C$_{20}$ alkyl group, a C$_1$ to C$_{20}$ alkoxy group, a C$_1$ to C$_{20}$ alkylamine group, a C$_1$ to C$_{20}$ alkylthio group, a C$_2$ to C$_{20}$ alkenyl group, a C$_2$ to C$_{20}$ alkynyl group, a C$_3$ to C$_{20}$ cycloalkyl group, a C$_6$ to C$_{20}$ aryl group, a C$_6$ to C$_{20}$ aryl group which is substituted with deuterium, a silane group, a boron group, a germanium group, and a C$_5$ to C$_{20}$ heterocyclic group, Y is hydrogen, deuterium, halogen, CN, NO$_2$, a C$_1$ to C$_{20}$ alkyl group, a C$_1$ to C$_{20}$ alkoxy group, a C$_1$ to C$_{20}$ alkylamine group, a C$_6$ to C$_{20}$ arylamine group, a C$_1$ to C$_{20}$ alkyl thio group, a C$_6$ to C$_{20}$ aryl thio group, a C$_1$ to C$_{20}$ alkyl thiophene group, a C$_6$ to C$_{20}$ aryl thiophene group, a C$_2$ to C$_{20}$ alkenyl group, a C$_2$ to C$_{20}$ alkynyl group, a C$_3$ to C$_{20}$ cycloalkyl group, a C$_6$ to C$_{20}$ aryl group, a C$_6$ to C$_{20}$ aryl group which is substituted with deuterium, a silane group which is unsubstituted or substituted with a alkyl group, a boron group, a germanium group which is unsubstituted or substituted with a alkyl group, or a C$_5$ to C$_{20}$ heterocyclic group, and Z is a C$_1$ to C$_{20}$ alkyl thio group, a C$_6$ to C$_{20}$ aryl thio group, a C$_1$ to C$_{20}$ alkyl thiophene group, a C$_6$ to C$_{20}$ aryl thiophene group, a C$_2$ to C$_{20}$ alkynyl group, a C$_3$ to C$_{20}$ cycloalkyl group, a silane group which is unsubstituted or substituted with a alkyl group, a boron group, a germanium group which is unsubstituted or substituted with a alkyl group.

2. The anthracene derivative according to claim 1, wherein R1 and R2 in the formula 1 are each independently a phenyl group, a phenyl group which is substituted with a C$_5$ to C$_{20}$ heterocyclic group, a phenyl group which is substituted with five deuteriums, a naphthyl group, a biphenyl group, a fluorenyl group, an anthracenyl group, a tetracenyl group, a pentacenyl group, a terphenyl group, a tetralinyl group, a stilbenzyl group, a carbazolylene group, a perylenyl group, a pyrenyl group, a phenathrenyl group, a triphenylenyl group, a crycenyl group, a pyridyl group, a bipyridyl group, a carbazole group, a thiophenyl group, a quinolinyl group, or an isoquinolinyl group.

3. The anthracene derivative according to claim 1, wherein X's in the formula 1 may be the same or different from each other, and are each independently a phenylene group, a phenylene group which is substituted with a C$_5$ to C$_{20}$ heterocyclic group, a phenylene group which is substituted with deuterium, a naphthylene group, a biphenylene group, a fluorenylene group, an anthracenylene group, a tetracenylene group, a pentacenylene group, a terphenylene group, a tetralinylene group, a stilbenzylene group, a carbazolylene group, a perylenylene group, a pyrenylene group, a phenathrenylene group, a triphenylenylene group, a crycenylene group, a pyridylene group, a bipyridylene group, a carbazole group, a thiophenylene group, a quinolinylene group, or an isoquinolinylene group.

4. The anthracene derivative according to claim 1, wherein Y in the formula 1 is hydrogen, deuterium, a C$_6$ to C$_{20}$ aryl group which is substituted with deuterium, a silane group which is unsubstituted or substituted with a alkyl group, a boron group, a germanium group which is unsubstituted or substituted with a alkyl group, or a C$_5$ to C$_{20}$ heterocyclic group, or a C$_6$ to C$_{20}$ aryl group.

5. The anthracene derivative according to claim 1, wherein Z in the formula 1 is a silane group which is unsubstituted or substituted with a alkyl group, a boron group, a germanium group which is unsubstituted or substituted with a alkyl group.

6. An anthracene derivative represented by a formula 1 is selected from the group consisting of the following structural formulae:

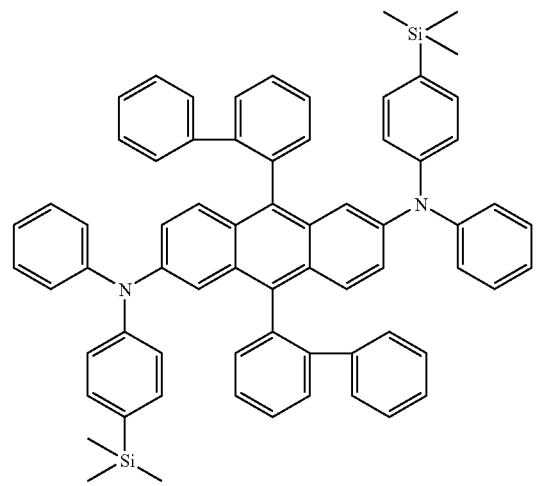

[Compound 1]

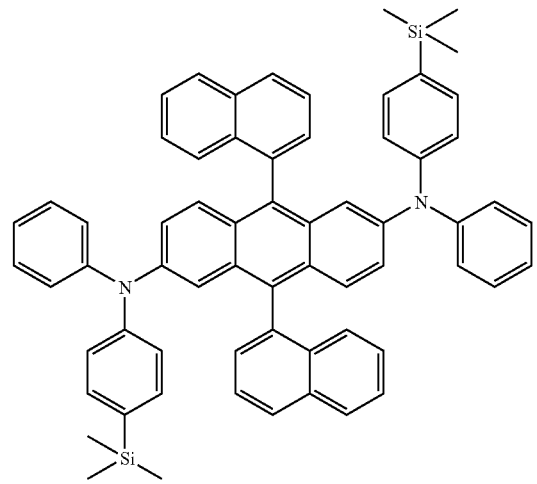

[Compound 2]

[Compound 3]
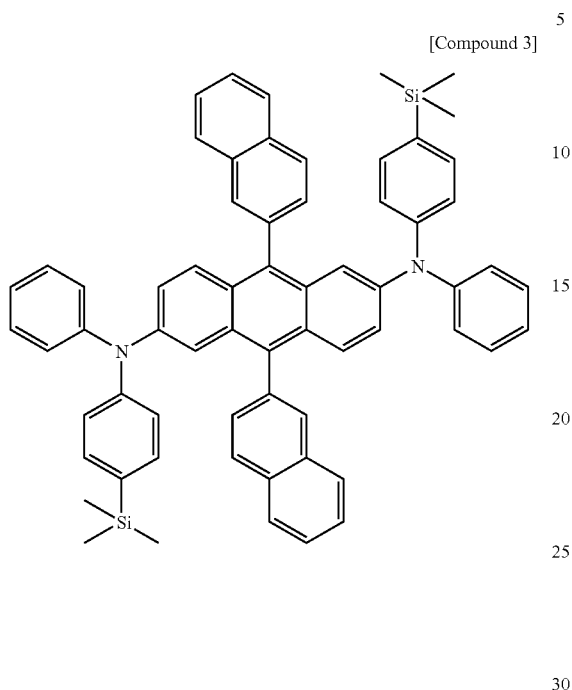
[Compound 5]
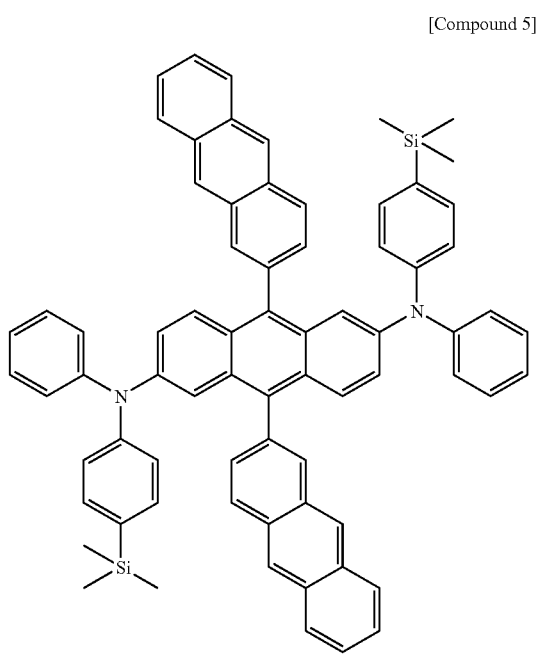
[Compound 4]
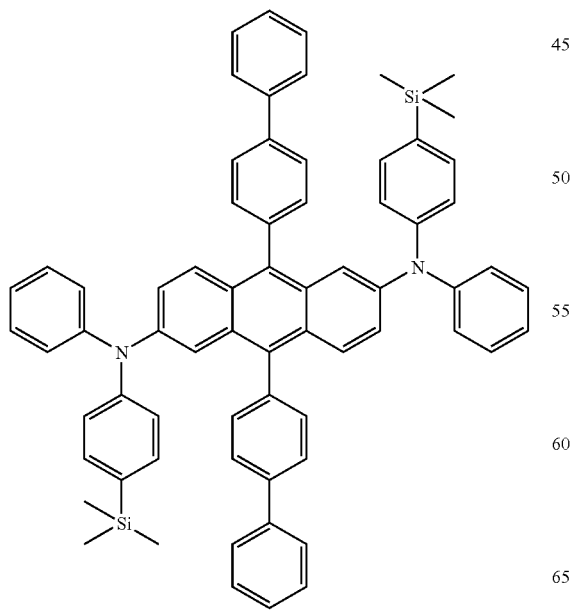
[Compound 6]
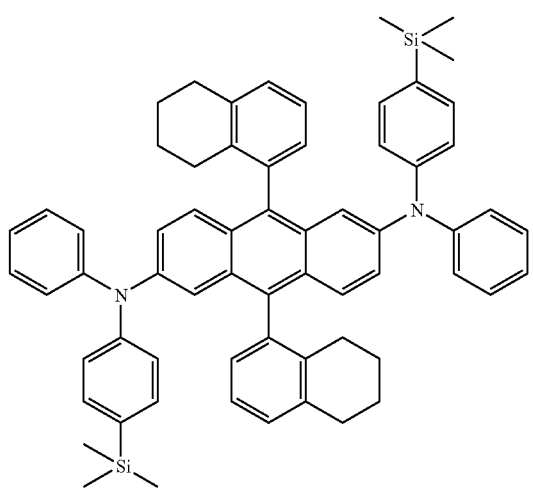

[Compound 7]
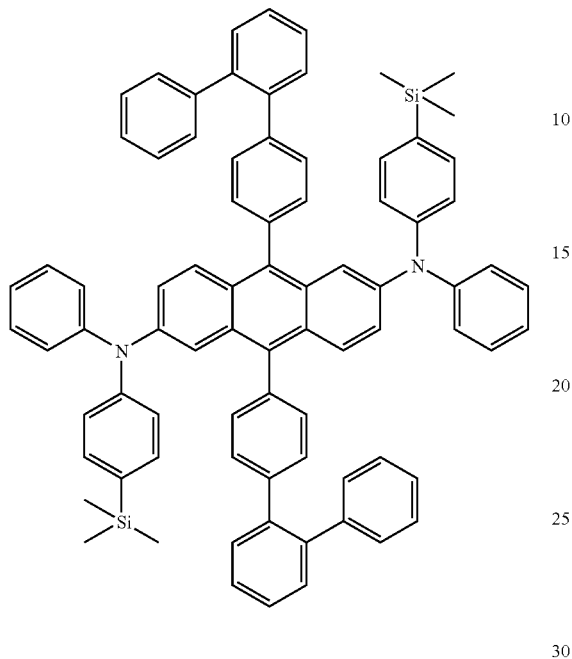
[Compound 9]
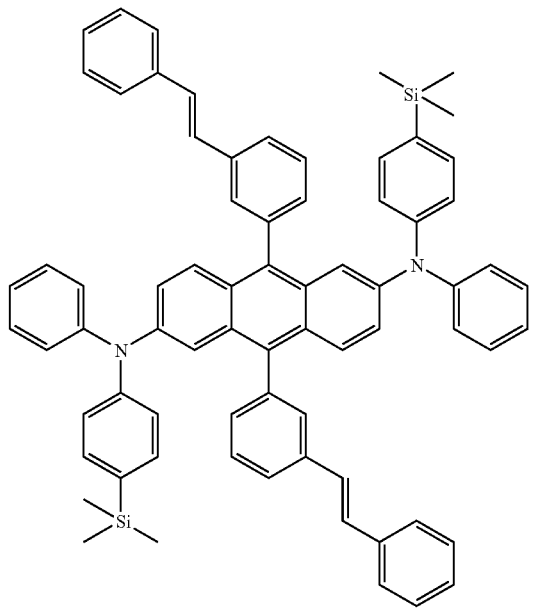
[Compound 8]
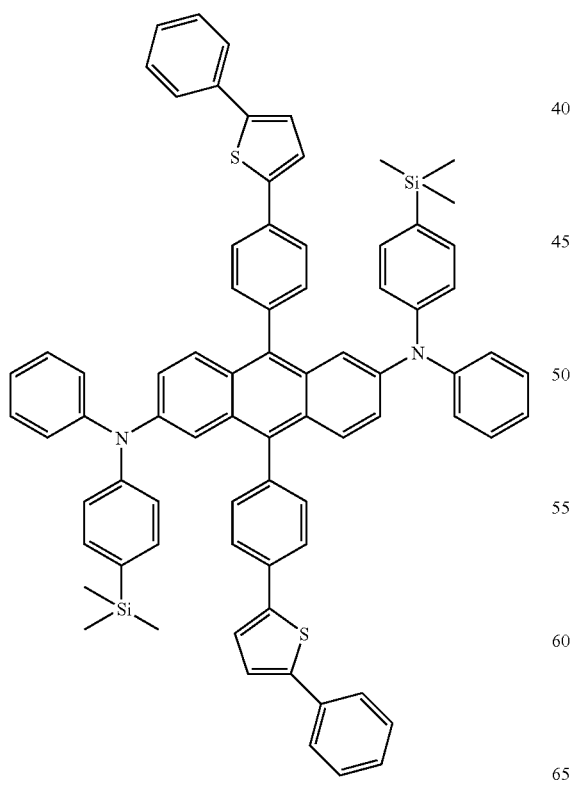
[Compound 10]
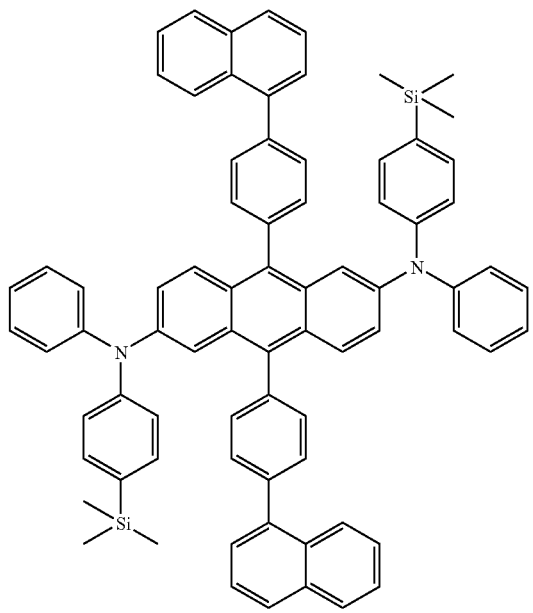

[Compound 11]
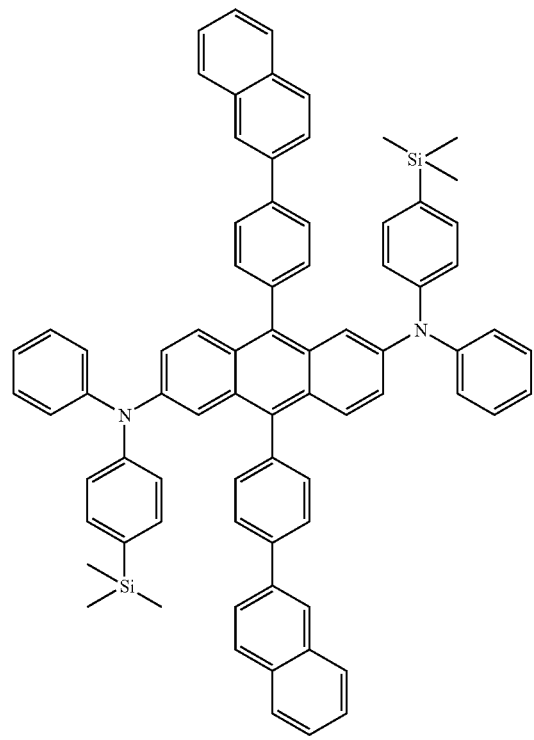
[Compound 12]
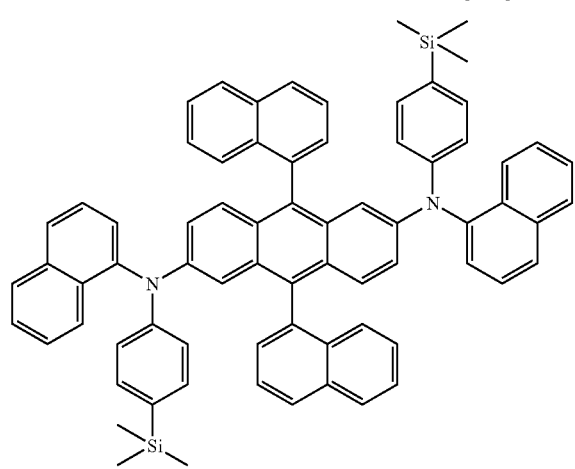
[Compound 13]
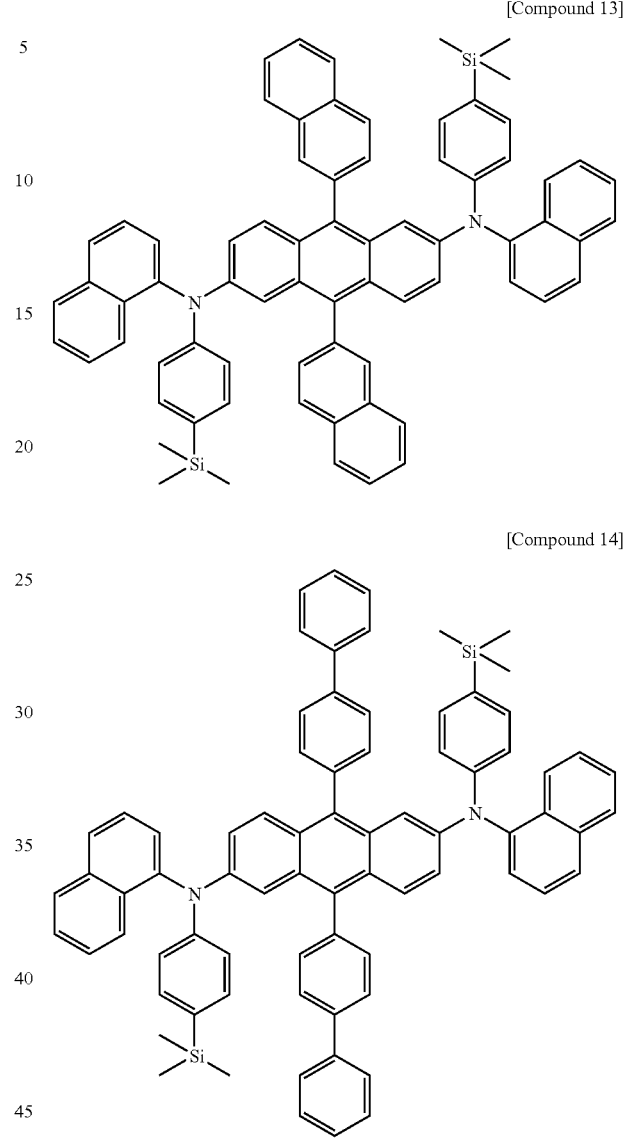
[Compound 14]
[Compound 15]
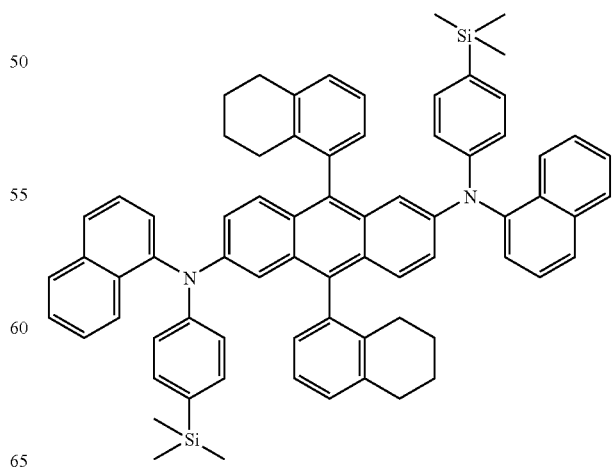

[Compound 16]
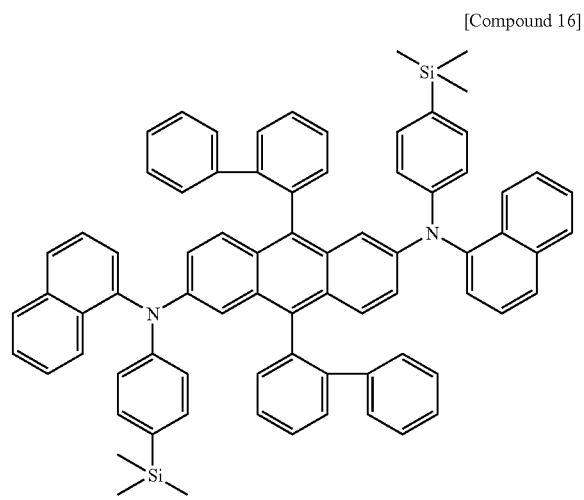
[Compound 17]
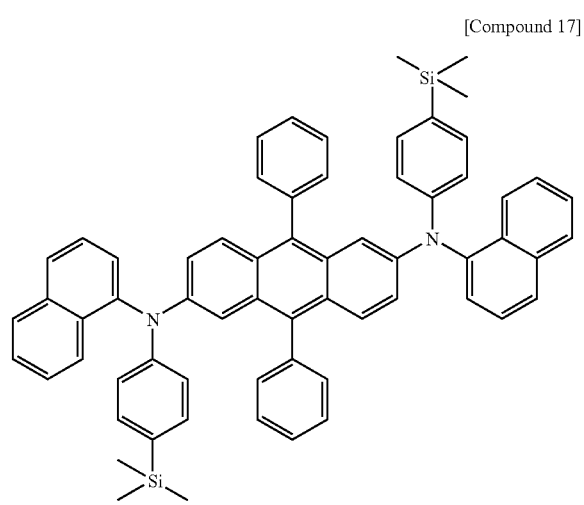
[Compound 18]
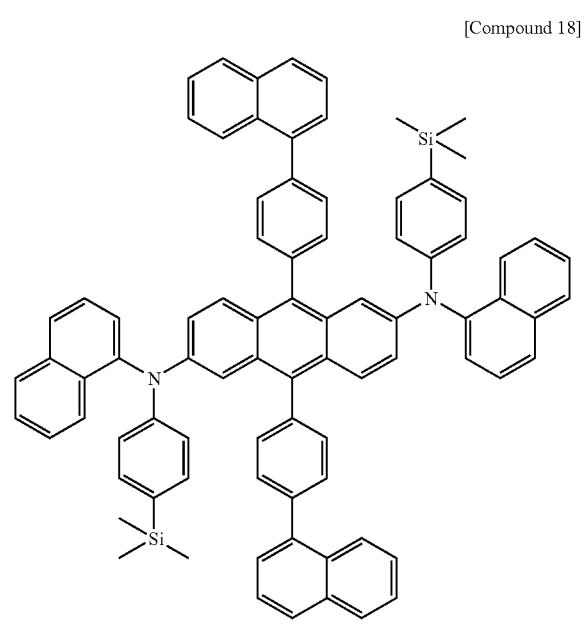
[Compound 19]
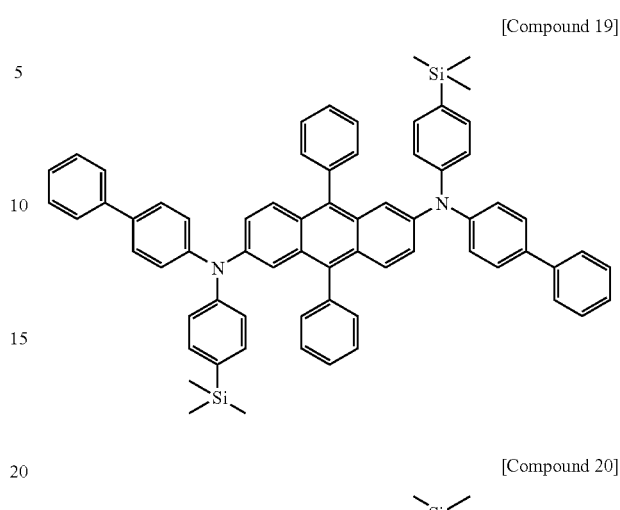
[Compound 20]
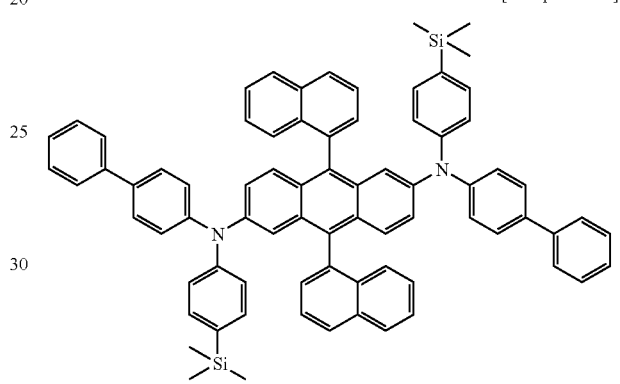
[Compound 21]
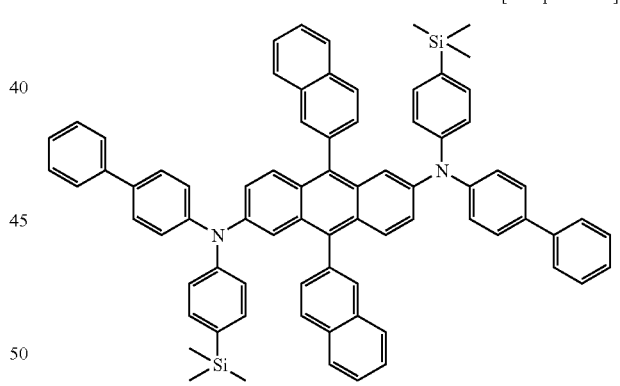
[Compound 22]
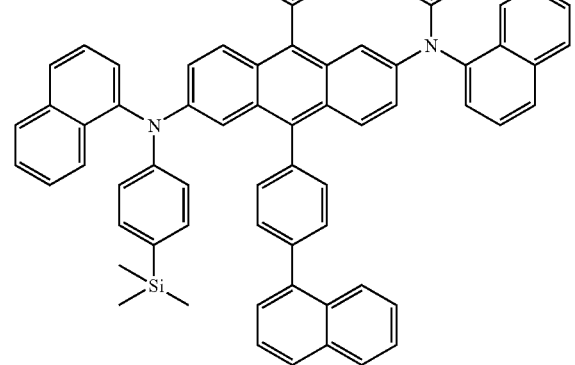

[Compound 23]
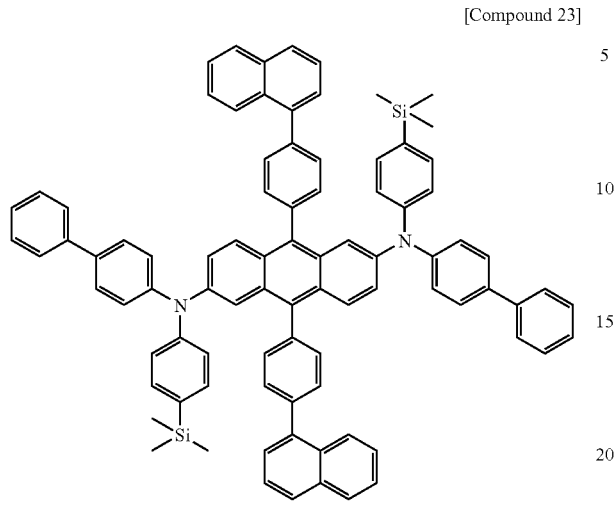
[Compound 26]
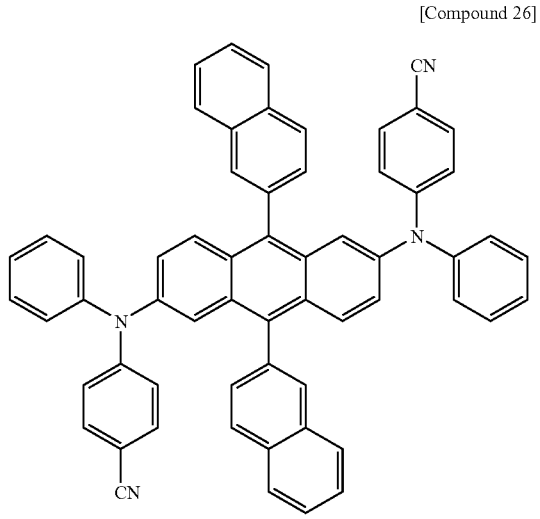
[Compound 24]
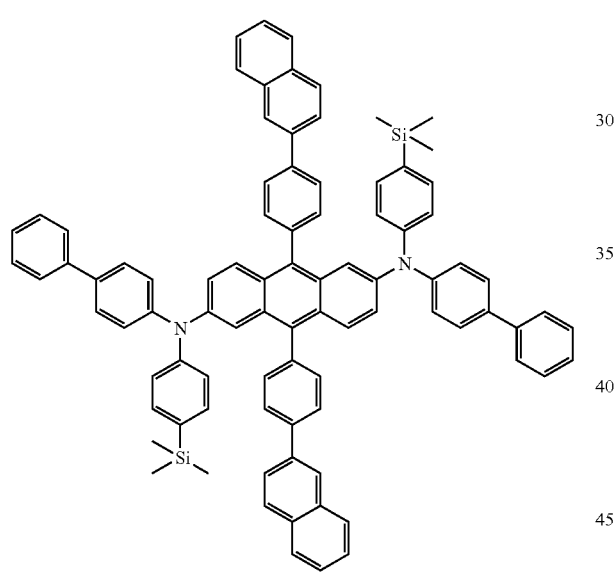
[Compound 27]
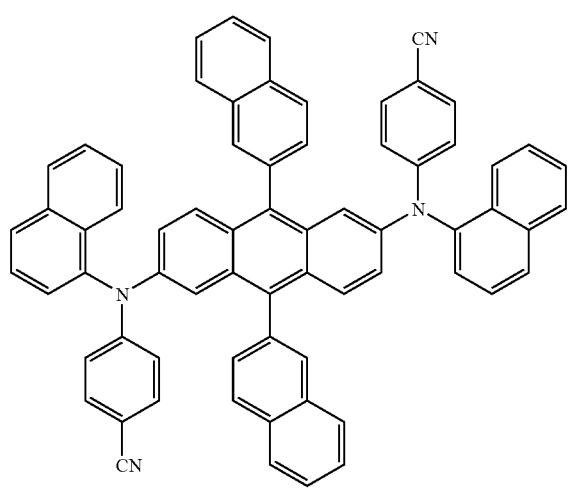
[Compound 25]
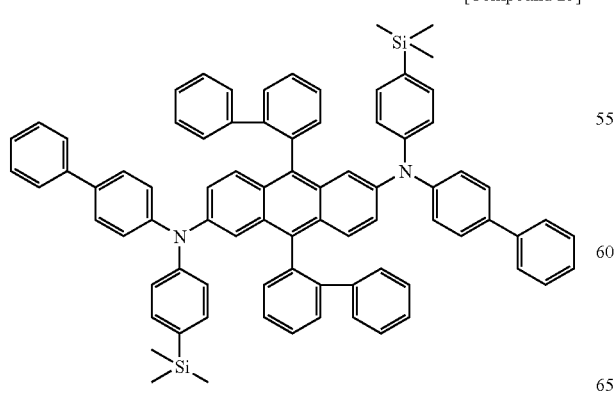
[Compound 28]
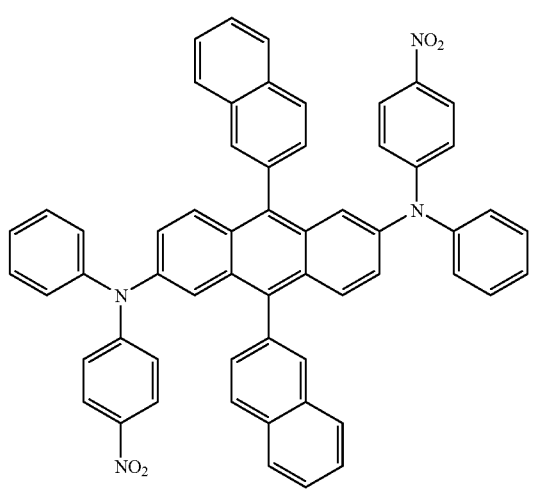

[Compound 29]
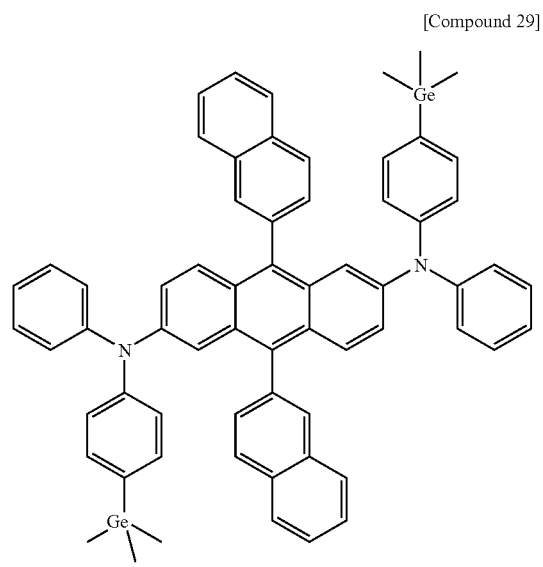
[Compound 30]
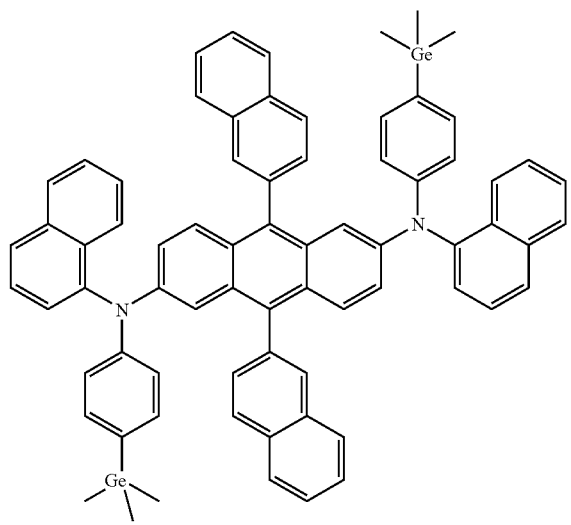
[Compound 31]
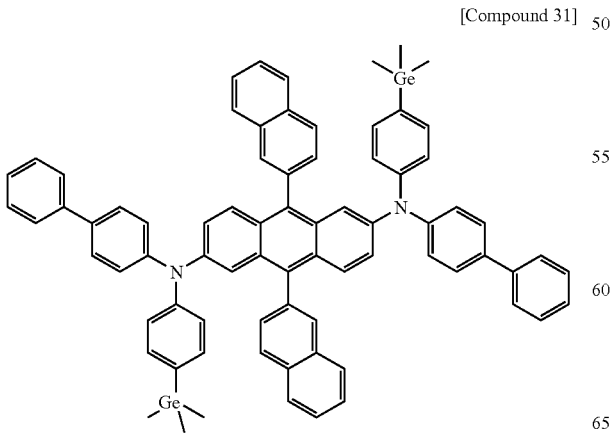
[Compound 32]
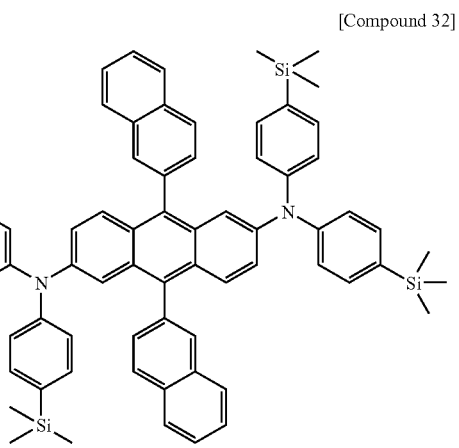
[Compound 33]
[Compound 34]
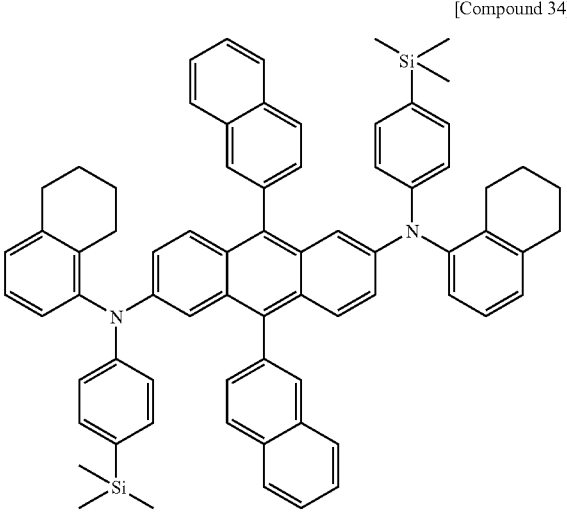

[Compound 35]

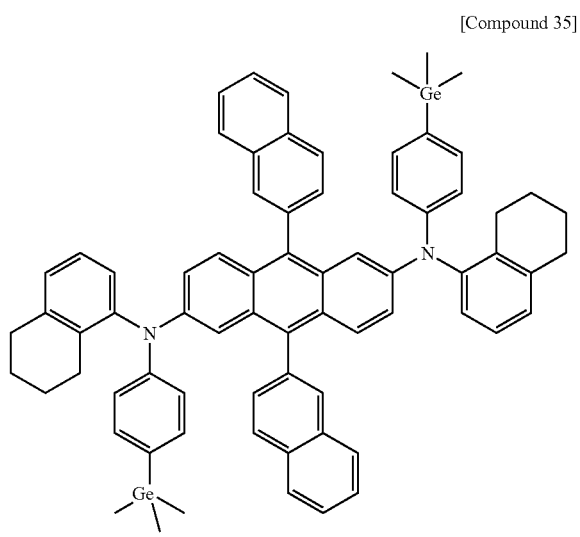

[Compound 38]

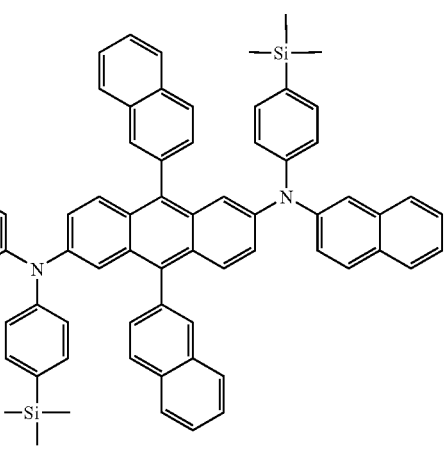

[Compound 36]

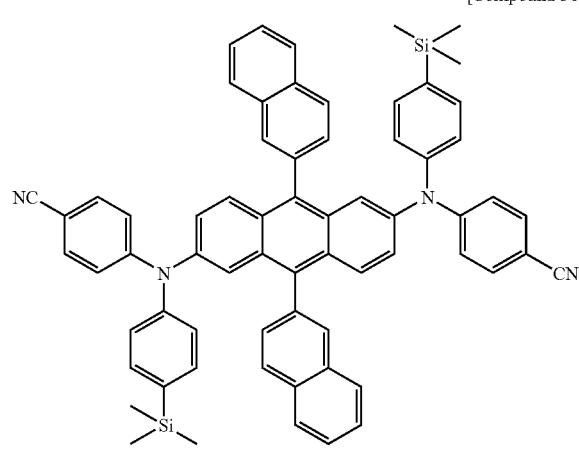

[Compound 39]

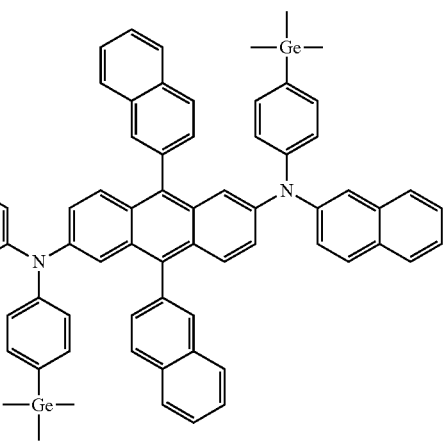

and

[Compound 44]

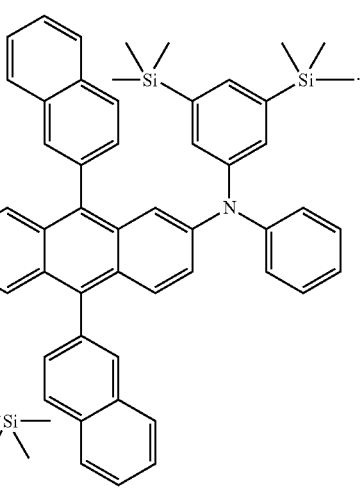

[Compound 37]

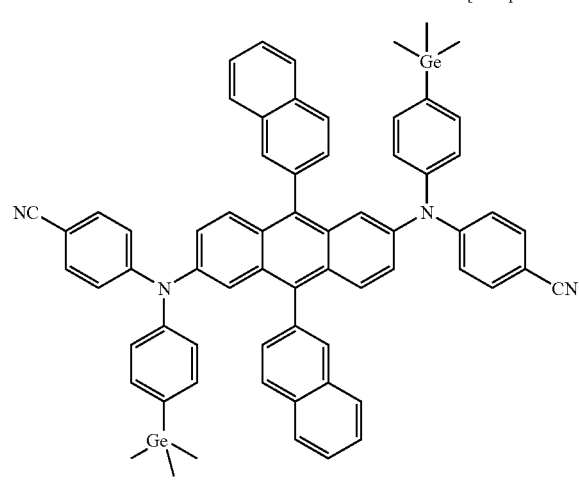

7. A process for preparing the anthracene according to claim 1, comprising the step of reacting a dibromoaryl compound with an arylamine compound in the presence of a palladium catalyst.

8. The process for preparing the anthracene according to claim 7, wherein the arylamine compound contains a silyl group, or a germanium group.

9. An organic electronic device comprising a first electrode, a second electrode, and one or more organic material layers interposed therebetween, wherein at least one layer of the organic material layers comprises the anthracene derivative according to claim 1.

10. The organic electronic device according to claim 9, wherein the organic material layers comprise at least one layer of a hole injecting layer, a hole transporting layer, and a hole injecting and hole transporting, and one layer of the layers comprises the anthracene derivative.

11. The organic electronic device according to claim 9, wherein the organic material layers comprise a light emitting layer, and the light emitting layer comprises the anthracene derivative.

12. The organic electronic device according to claim 9, wherein the organic material layers comprise an electron transporting layer, and the electron transporting layer comprises the anthracene derivative.

13. The organic electronic device according to claim 9, wherein the organic electronic device is selected from the group consisting of an organic light emitting device, an organic solar cell, an organic photoconductor (OPC), and an organic transistor.

14. An organic electronic device comprising a first electrode, a second electrode, and one or more organic material layers interposed therebetween, wherein at least one layer of the organic material layers comprises the anthracene derivative according to claim 6.

15. The organic electronic device according to claim 14, wherein the organic material layers comprise at least one layer of a hole injecting layer, a hole transporting layer, and a hole injecting and hole transporting, and one layer of the layers comprises the anthracene derivative.

16. The organic electronic device according to claim 14, wherein the organic material layers comprise a light emitting layer, and the light emitting layer comprises the anthracene derivative.

17. The organic electronic device according to claim 14, wherein the organic material layers comprise an electron transporting layer, and the electron transporting layer comprises the anthracene derivative.

18. The organic electronic device according to claim 14, wherein the organic electronic device is selected from the group consisting of an organic light emitting device, an organic solar cell, an organic photoconductor (OPC), and an organic transistor.

* * * * *